(12) United States Patent
Bancel et al.

(10) Patent No.: US 12,390,278 B2
(45) Date of Patent: Aug. 19, 2025

(54) SYSTEMS AND METHODS FOR ADAPTIVE ABLATION VOLUME PREDICTION BASED ON TISSUE TEMPERATURE MEASUREMENTS AND ANATOMICAL SEGMENTATION

(71) Applicant: Hepta Medical SAS, Suresnes (FR)

(72) Inventors: Thomas Bancel, Saint Cloud (FR); Matteo Bonhomme, Paris (FR); Nadir El Fassi, Vigneux sur Seine (FR)

(73) Assignee: Hepta Medical SAS, Suresnes (FR)

( * ) Notice: Subject to any disclaimer, the term of this patent is extended or adjusted under 35 U.S.C. 154(b) by 0 days.

(21) Appl. No.: 18/932,414

(22) Filed: Oct. 30, 2024

(65) Prior Publication Data

US 2025/0134596 A1    May 1, 2025

Related U.S. Application Data

(60) Provisional application No. 63/595,306, filed on Nov. 1, 2023.

(30) Foreign Application Priority Data

Oct. 31, 2023    (EP) ..................................... 23306887

(51) Int. Cl.
*A61B 18/12*    (2006.01)
*A61B 18/18*    (2006.01)
(Continued)

(52) U.S. Cl.
CPC .......... *A61B 34/10* (2016.02); *A61B 18/1815* (2013.01); *A61B 2017/00039* (2013.01);
(Continued)

(58) Field of Classification Search
CPC . A61B 18/18; A61B 18/1815; A61B 18/1206; A61B 18/1233;
(Continued)

(56) References Cited

U.S. PATENT DOCUMENTS 4,190,053 A    2/1980 Sterzer
4,240,445 A    12/1980 Iskander et al.
(Continued)

FOREIGN PATENT DOCUMENTS

CN    205073020 U    3/2016
EP    2299540 B1    1/2013
(Continued)

OTHER PUBLICATIONS

International Search Report & Written Opinion dated Jun. 22, 2021 in Int'l. PCT Patent Appl. Serial No. PCT/IB2021/050682.
(Continued)

*Primary Examiner* — Thomas A Giuliani
(74) *Attorney, Agent, or Firm* — Greenberg Traurig, LLP; Christopher C. Bolten; Albert K. Heng

(57) ABSTRACT

Systems and methods for ablating target tissue, measuring parameters during ablation such as temperature of the target tissue, and predicting volume of the ablation based on the measured parameters are provided. The system may include a switching antenna for both heating of target tissue and radiometry to monitor the temperature of the heated tissue, and a processor for calculating the temperature of the target tissue, segmenting medical images, and predicting volume of the ablation based on radiometric signals indicative of the target tissue temperature. The predicted ablation volume may be adapted to account for tissue boundaries and anatomical structures. The processor further may determine properties of the target tissue such as tissue type.

30 Claims, 18 Drawing Sheets

(51) Int. Cl.
*A61B 34/10* (2016.01)
*A61B 17/00* (2006.01)
*A61B 18/00* (2006.01)

(52) U.S. Cl.
CPC .............. *A61B 2017/00199* (2013.01); *A61B 2018/00404* (2013.01); *A61B 2018/00577* (2013.01); *A61B 2018/00803* (2013.01); *A61B 2034/104* (2016.02)

(58) Field of Classification Search
CPC .. A61B 2018/1823; A61B 2018/00577; A61B 2018/00803; A61B 2018/00636; A61B 2018/00642; A61B 2018/00684; A61B 2018/00791; A61B 34/10; A61B 2017/00039; A61B 2017/00199; A61B 2034/104
USPC ................. 606/32–34, 38, 42; 607/101, 102
See application file for complete search history.

(56) References Cited

U.S. PATENT DOCUMENTS

| | | | |
|---|---|---|---|
| 5,344,435 A | 9/1994 | Turner et al. | |
| 5,886,589 A | 3/1999 | Mourant | |
| 6,485,486 B1 | 11/2002 | Trembly et al. | |
| 6,635,055 B1 | 10/2003 | Cronin | |
| 7,699,841 B2 | 4/2010 | Carr | |
| 7,769,469 B2 | 8/2010 | Carr et al. | |
| 8,926,605 B2 | 1/2015 | McCarthy et al. | |
| 8,932,284 B2 | 1/2015 | McCarthy et al. | |
| 8,961,506 B2 | 2/2015 | McCarthy et al. | |
| 8,964,605 B1 | 2/2015 | Ansari | |
| 9,226,791 B2 | 1/2016 | McCarthy et al. | |
| 9,277,961 B2 | 3/2016 | Panescu et al. | |
| 9,861,440 B2 | 1/2018 | Van Der Weide et al. | |
| 9,872,729 B2 | 1/2018 | Van Der Weide et al. | |
| 9,956,038 B2 | 5/2018 | Allison | |
| 11,337,756 B2 | 5/2022 | Allison | |
| 11,622,807 B2 | 4/2023 | Crozier et al. | |
| 12,064,174 B2 | 8/2024 | Allison et al. | |
| 12,161,403 B2 | 12/2024 | Allison | |
| 2004/0243004 A1 | 12/2004 | Carr | |
| 2004/0249272 A1 | 12/2004 | Carr | |
| 2006/0121873 A1 | 6/2006 | Ammar | |
| 2009/0187180 A1 | 7/2009 | Brannan | |
| 2009/0196480 A1* | 8/2009 | Nields | G06T 7/33 382/132 |
| 2011/0066147 A1* | 3/2011 | He | A61B 18/1492 606/33 |
| 2011/0208177 A1 | 8/2011 | Brannan | |
| 2012/0029359 A1 | 2/2012 | Sterzer et al. | |
| 2012/0239030 A1* | 9/2012 | Ladtkow | A61B 18/1815 606/41 |
| 2013/0041365 A1 | 2/2013 | Rusin et al. | |
| 2013/0281851 A1 | 10/2013 | Carr | |
| 2013/0317499 A1 | 11/2013 | Brannan et al. | |
| 2013/0324993 A1 | 12/2013 | McCarthy et al. | |
| 2013/0345693 A1 | 12/2013 | Brannan | |
| 2013/0345697 A1* | 12/2013 | Garcia | A61B 18/1477 606/34 |
| 2014/0303614 A1 | 10/2014 | McCarthy et al. | |
| 2015/0105765 A1 | 4/2015 | Panescu et al. | |
| 2015/0290465 A1 | 10/2015 | Mashiach | |
| 2016/0030111 A1 | 2/2016 | Ladtkow et al. | |
| 2016/0345896 A1 | 12/2016 | Allison | |
| 2017/0105798 A1 | 4/2017 | Allison | |
| 2017/0172655 A1 | 6/2017 | Allison et al. | |
| 2018/0078309 A1 | 3/2018 | Van Der Weide et al. | |
| 2018/0125579 A1 | 5/2018 | Van Der Weide et al. | |
| 2019/0090948 A1 | 3/2019 | Dickhans | |
| 2019/0365466 A1 | 12/2019 | Allison | |
| 2019/0380777 A1 | 12/2019 | Huang et al. | |
| 2020/0069368 A1 | 3/2020 | Huang et al. | |
| 2020/0305974 A1 | 10/2020 | Brannan et al. | |
| 2021/0236202 A1* | 8/2021 | Allison | A61B 5/6852 |
| 2022/0125511 A1 | 4/2022 | Crozier et al. | |
| 2022/0280232 A1 | 9/2022 | Allison | |

FOREIGN PATENT DOCUMENTS

| | | |
|---|---|---|
| EP | 2777591 A1 | 9/2014 |
| EP | 3456279 A1 | 3/2019 |
| JP | 2022089125 A | 6/2022 |
| WO | WO-02061880 A2 | 8/2002 |
| WO | WO-2006127847 A2 | 11/2006 |
| WO | WO-2007025198 A2 | 3/2007 |
| WO | WO-2010048334 A1 | 4/2010 |
| WO | WO-2010085329 A1 | 7/2010 |
| WO | WO-2010085529 A1 | 7/2010 |
| WO | WO-2012007854 A1 | 1/2012 |
| WO | WO-2013192553 A1 | 12/2013 |
| WO | WO-2014025549 A1 | 2/2014 |
| WO | WO-2014138410 A1 | 9/2014 |
| WO | WO-2015004420 A1 | 1/2015 |
| WO | WO-2016018546 A1 | 2/2016 |
| WO | WO-2016033090 A1 | 3/2016 |
| WO | WO-2016054156 A1 | 4/2016 |
| WO | WO-2016089887 A1 | 6/2016 |
| WO | WO-2016197093 A1 | 12/2016 |
| WO | WO-2017173523 A1 | 10/2017 |
| WO | WO-2017181182 A1 | 10/2017 |
| WO | WO-2018140816 A1 | 8/2018 |
| WO | WO-2019231936 A1 | 12/2019 |
| WO | WO-2020033998 A1 | 2/2020 |
| WO | WO-2020033999 A1 | 2/2020 |
| WO | WO-2020188249 A1 | 9/2020 |
| WO | WO-2022051654 A1 | 3/2022 |

OTHER PUBLICATIONS

International Search Report and Written Opinion dated Aug. 26, 2019 in Int'l. PCT Patent Appl. Serial No. PCT/US2019/034226.
International Search Report & Written Opinion dated Mar. 28, 2025 in Int'l PCT Patent Appl. Serial No. PCT/IB2024/060723.

* cited by examiner

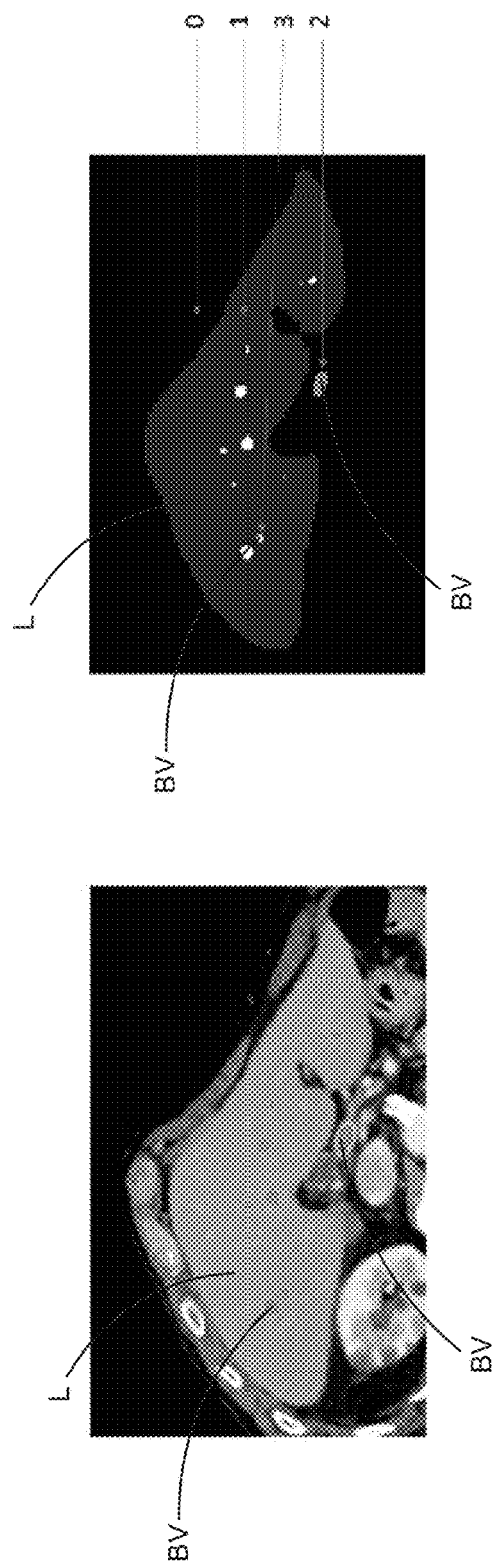
FIG. 11A
FIG. 11B
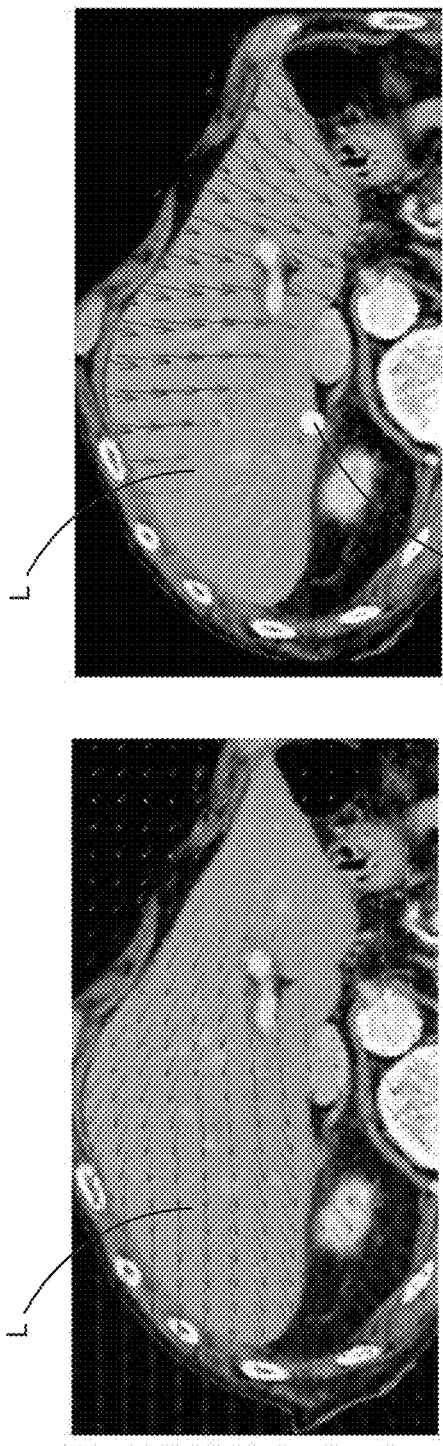
FIG. 11C
FIG. 11D

SYSTEMS AND METHODS FOR ADAPTIVE ABLATION VOLUME PREDICTION BASED ON TISSUE TEMPERATURE MEASUREMENTS AND ANATOMICAL SEGMENTATION

CROSS-REFERENCE TO RELATED APPLICATIONS

This application claims priority to U.S. Provisional Patent Application No. 63/595,306, filed Nov. 1, 2023, and European Patent Application No. 23306887.3, filed Oct. 31, 2023, the entire contents of each of which are incorporated herein by reference.

FIELD OF USE

The present disclosure is directed to systems and methods for safe and efficacious ablation of target tissue by, for example, measuring parameters during ablation such as temperature of the target tissue, as well as predicting volume of the ablation based on the measured parameters.

BACKGROUND

Tissue ablation may be used to treat a variety of clinical disorders and several ablation techniques have been developed, including cryoablation, microwave ablation, radio frequency (RF) ablation, and ultrasound ablation. Such techniques are typically performed by a clinician who introduces a catheter having an ablative tip to the target tissue percutaneously, or via the venous vasculature or the natural cavities, positions the ablative tip adjacent to what the clinician believes to be an appropriate region based on tactile feedback, mapping electrocardiogram (ECG) signals, anatomy, and/or fluoroscopic imaging, actuates flow of an irrigant to cool the surface of the selected region, and then actuates the ablative tip for a period of time believed sufficient to destroy tissue in the selected region.

Although commercially available ablative tips may include thermocouples for providing temperature feedback via a digital display, such thermocouples typically do not provide meaningful temperature feedback during irrigated ablation. For example, the thermocouple only measures surface temperature, whereas the heating or cooling of the tissue that results in tissue ablation may occur at some depth below the tissue surface. Moreover, for procedures in which the surface of the tissue is cooled with an irrigant, the thermocouple will measure the temperature of the irrigant, thus further obscuring any useful information about the temperature of the tissue, particularly at depth. As such, the clinician has no useful feedback regarding the temperature of the tissue as it is being ablated or whether the time period of the ablation is sufficient. Accordingly, it would be desirable to provide thermocouple configurations at the ablative tip that permit a high degree of tissue temperature measurement to achieve accurate temperature measurement with microwave heating.

Accordingly, it may only be revealed after the procedure is completed, that the targeted aberrant pathway was not adequately destroyed. In such a circumstance, the clinician may not know whether the procedure failed because the incorrect region of tissue was ablated, because the ablative tip was not actuated for a sufficient period of time to destroy the target tissue, because the ablative tip was not touching or insufficiently touching the tissue, because the power of the ablative energy was insufficient, or some combination of the above. Upon repeating the ablation procedure so as to again attempt to ablate the target tissue, the clinician may have as little feedback as during the first procedure, and thus potentially may again fail to destroy the aberrant pathway. Additionally, there may be some risk that the clinician would re-treat a previously ablated region of the target tissue and not only ablate the target tissue, but damage adjacent tissues.

In some circumstances, to avoid having to repeat the ablation procedure as such, the clinician may ablate a series of regions of the target tissue along which the target tissue is believed to lie, so as to improve the chance of successful ablation. However, there is again insufficient feedback to assist the clinician in determining whether any of those ablated regions are sufficiently destroyed. Despite the promise of precise temperature measurement sensitivity and control offered by the use of radiometry, there have been few successful commercial medical applications of this technology. One drawback of previously-known systems has been an inability to obtain highly reproducible results due to slight variations in the construction of the microwave antenna used in the radiometer, which can lead to significant differences in measured temperature from one catheter to another. Problems also have arisen with respect to orienting the radiometer antenna on the catheter to adequately capture the radiant energy emitted by the tissue, and with respect to shielding high frequency microwave components in the surgical environment so as to prevent interference between the radiometer components and other devices in the surgical field.

Acceptance of microwave-based hyperthermia treatments and temperature measurement techniques also has been impeded by the capital costs associated with implementing radiometric temperature control schemes. Radiofrequency ablation techniques have developed a substantial following in the medical community, even though such systems can have severe limitations, such as the inability to accurately measure tissue temperature at depth, e.g., where irrigation is employed. However, the widespread acceptance of RF ablation systems, extensive knowledge base of the medical community with such systems, and the significant cost required to changeover to, and train for, newer technologies has dramatically retarded the widespread adoption of radiometry.

U.S. Pat. Nos. 8,926,605 and 8,932,284 to McCarthy et al., the entire contents of each of which are incorporated herein by reference, describe systems for radiometrically measuring temperature during ablation.

In view of the foregoing, it would be desirable to provide systems and methods that permit a high degree of radiometric measurement of temperature at depth in tissue to achieve accurate temperature measurement with microwave heating.

In addition, it would be desirable to use such accurate radiometric temperature measurements to predict the volume of ablation of the target tissue in real-time as a feedback mechanism for detecting and/or preventing overheating of target tissue during an ablation procedure, as well as to inform additional properties of the target tissue such as tissue type and/or other physical properties.

While there is a breadth of energy-based devices to treat a range of conditions, giving promise of improved outcomes, lower risks and shortened recovery times, there remains significant opportunity to exploit capabilities of distinct technologies to deliver optimal therapy to drive outcome and improve risk profiles.

SUMMARY

The present disclosure overcomes the drawbacks of previously-known systems and methods by providing a system for predicting ablation volume of tissue. The system may comprise a controller having instructions that, when executed by one or more processors of the controller, cause the controller to: receive information indicative of temperature of a tissue being ablated via an antenna; extract one or more features of the temperature of the tissue from the information, the one or more features comprising at least one of an area under a curve of the temperature of the tissue, a maximum temperature of the tissue, a thermal dose of the temperature of the tissue, an initial slope of the temperature of the tissue, or an average temperature rise of the tissue; and execute an ablation volume prediction algorithm to predict the volume of ablation of the tissue based on the extracted one or more features and a trend line derived from a correlated dataset of ablation volumes associated with the extracted one or more features.

The information indicative of temperature of the tissue being ablated via the antenna may comprise a radiometric signal generated by the antenna. Accordingly, the system may be configured to use an anti-spike filter on the radiometric signal to remove one or more incorrect points within the radiometric signal. For example, the anti-spike filter may comprise at least one of a moving minimum or an algorithm based on a first derivative. Moreover, the system may be configured to use a smoothing filter on the radiometric signal to generate a smoother signal. For example, the smoothing filter may comprise at least one of a Kalman filter or a moving average. In addition, the system may be configured to detect an uncontrolled increase in temperature of the tissue based on the radiometric signal. The system further may be configured to detect a presence of a heat sink based on the radiometric signal and a dataset of simulation results. Additionally, or alternatively, the information indicative of temperature of the tissue being ablated via the antenna may comprise a voltage returned by a thermocouple disposed on an external surface of the antenna.

In addition, the system may be configured to take a logarithm of cumulative equivalent minutes at 43° C. to extract the thermal dose of the tissue. The system further may be configured to calculate a short axis and a long axis of an ellipsoidal ablation volume corresponding with the predicted volume of ablation of the tissue, the long axis parallel to a longitudinal axis of the antenna. For example, the system may be configured to calculate the short axis of the ellipsoidal ablation volume based on the extracted thermal dose and a trend line derived from a correlated dataset of short axes associated with the extracted thermal dose. Additionally, or alternatively, the system may be configured to calculate the short axis and the long axis of the ellipsoidal ablation volume based on an aspect ratio of the predicted volume of ablation of the tissue.

The system also may be configured to: compare the extracted initial slope of the temperature of the tissue with a dataset of initial slope values and associated electromagnetic tissue properties to determine one or more electromagnetic properties of the tissue; and determine a type of the tissue based on the determined one or more electromagnetic properties of the tissue. For example, the system may be configured to determine whether the tissue is healthy tissue or cancerous tissue based on the determined one or more electromagnetic properties of the tissue. Moreover, the system may be configured to cause the antenna to emit energy to the tissue at a predetermined level for a predetermined time period, such that the predetermined level and the predetermined time period are insufficient to damage the tissue. Accordingly, the initial slope of the temperature of the tissue may be extracted from the information, e.g., the radiometric signal or the voltage returned by the thermocouple, received responsive to the energy emitted to the tissue at the predetermined level for the predetermined time period. The system further may be configured to estimate one or more tissue property parameters of the tissue based on the information indicative of temperature of the tissue being ablated and a correlated dataset of tissue temperatures and corresponding average tissue property parameter values, and adapt the predicted volume of ablation of the tissue based on the one or more tissue property parameters.

In addition, the system may be configured to determine at least one of water content of the tissue or physical properties of surrounding tissue based on the extracted initial slope of the temperature of the tissue. Further, the system may be configured to cause a display to display the predicted volume of ablation of the tissue. For example, the system may be configured to: receive a medical image comprising the tissue and the antenna; execute a segmentation algorithm to segment the tissue and the antenna in the medical image; label the segmented tissue and antenna on the medical image; and cause the display to display the predicted volume of ablation of the tissue overlaid on the labeled medical image comprising the labeled segmented tissue and antenna. The medical image may comprise a CT scan image, a CBCT scan image, a tomosynthesis image based on X-ray, an MRI image, or an echographic B-mode image.

Moreover, the system may be configured to: receive a pre-operative medical image comprising the tissue, the pre-operative medical image comprising a labeled lesion; execute a segmentation algorithm to segment the tissue in the pre-operative medical image; execute a registration toolbox to register the labeled medical image and the pre-operative medical image based on the segmented tissue in the labeled medical image and the pre-operative medical image; and overlay the labeled lesion on the registered labeled medical image. Accordingly, the displayed predicted volume of ablation of the tissue may be overlaid on the registered labeled medical image comprising the labeled lesion.

The medical image may comprise one or more anatomical structures, e.g., at least one of an airway, a blood vessel, or bile ducts. Accordingly, the system may be configured to: execute a segmentation algorithm to segment the one or more anatomical structures in the medical image; and label the segmented one or more anatomical structures on the medical image. Thus, the displayed predicted volume of ablation of the tissue may be overlaid on the labeled medical image comprising the labeled segmented tissue, antenna, and one or more anatomical structures. In addition, the system may be configured to: determine a boundary of the tissue based on the segmented tissue; and determine a shape of the predicted volume of ablation of the tissue based on the boundary of the tissue, a location of the segmented antenna, a location of the segmented one or more anatomical structures, and a dataset of simulation results. Accordingly, the displayed predicted volume of ablation of the tissue may comprise the determined shape.

The segmentation algorithm may be configured to: threshold the medical image with an adaptive threshold based on the medical image; compute one or more connected components of the thresholded medical image; discard any one of the one or more connected components smaller than a predetermined size; compute a straightness index for each of the remaining one or more connected components; and classify the connected component with the lowest straightness index as the antenna. For example, the segmentation algorithm may be configured to: (a) select three random points on each of the remaining one or more connected components; (b) calculate an angle between the three random points of each of the remaining one or more connected components; (c) determine a value based on a minimum of an extra-angle and the angle for each of the remaining one or more connected components; (d) repeat (a) to (c) a plurality of times; and (e) compute the straightness index for each of the remaining one or more connected components as an average of the determined values.

Moreover, the system may be configured to simulate growth of the predicted volume of ablation of the tissue over time. For example, the system may be configured to create a patient specific simulation simulating growth of the predicted volume of ablation of the tissue over time. In addition, the system further may be configured to compute a contraction of the tissue based on a registration of pre-operative and post-operative scans of the tissue, and adapt the patient specific simulation based on the contraction of the tissue. For example, the system further may be configured to: execute a segmentation algorithm to segment the tissue and one or more anatomical structures within the pre-operative and post-operative scans; convert the segmented tissue and one or more anatomical structures within the pre-operative and post-operative scans to a binary mask to create custom volumes of the pre-operative and post-operative scans; register the custom volume of the pre-operative scans with the custom volume of the post-operative scans; and force displacement of the voxels at the antenna to zero to compute the contraction of the tissue.

Additionally, the system further may be configured to: receive medical images comprising the tissue, one or more anatomical structures within the tissue, and the antenna; execute a segmentation algorithm to segment the tissue, the one or more anatomical structures, and the antenna in the medical images; crop predetermined volumes of the tissue and the one or more anatomical structures from the segmented medical images based on a position of the antenna within the segmented medical images; and smooth the cropped volumes of the tissue and the one or more anatomical structures. Accordingly, the patient specific simulation may be created based on the cropped and smoothed volumes of the tissue and the one or more anatomical structures. Moreover, the system may be configured to compute one or more connected components of the cropped volumes of the tissue and the one or more anatomical structures, and discard any one of the one or more connected components smaller than a predetermined size, such that the cropped and smoothed volumes of the tissue and the one or more anatomical structures may comprise only the one or more connected components larger than the predetermined size.

For example, the one or more anatomical structures may comprise one or more blood vessels, and the medical images may comprise pre-operative medical images comprising the tissue and the one or more blood vessels and per-operative medical images obtained during an ablation procedure that comprise the tissue and the antenna. Accordingly, the system may further be configured to register the one or more blood vessels from the pre-operative medical images to the per-operative medical images to crop the predetermined volume of the blood vessels based on the position of the antenna. The predetermined cropped volume of the blood vessels may be smaller than the predetermined cropped volume of the tissue. Moreover, the system may be configured to determine a shape of the predicted volume of ablation of the tissue at least partially based on the patient specific simulation. The ablation volume prediction algorithm may be configured to predict the volume of ablation of the tissue based on a power level of energy used to ablate the tissue.

In accordance with another aspect of the present disclosure, a system for determining a type of tissue is provided. The system may comprise a controller having instructions that, when executed by one or more processors of the controller, cause the controller to: receive a radiometric signal indicative of temperature of a tissue receiving energy via an antenna; extract an initial slope of the temperature of the tissue from the radiometric signal; compare the extracted initial slope of the temperature of the tissue with a dataset of initial slope values and associated electromagnetic tissue properties to determine one or more electromagnetic properties of the tissue; and determine a type of the tissue based on the determined one or more electromagnetic properties of the tissue. Moreover, the system may be configured to determine whether the tissue is healthy tissue or cancerous tissue based on the determined one or more electromagnetic properties of the tissue. In addition, the system may be configured to cause the antenna to emit energy to the tissue at a predetermined level for a predetermined time period, such that the predetermined level and the predetermined time period are insufficient to damage the tissue. Accordingly, the initial slope of the temperature of the tissue may be extracted from the radiometric signal received responsive to the energy emitted to the tissue at the predetermined level for the predetermined time period.

BRIEF DESCRIPTION OF THE DRAWINGS

FIGS. 11A to 11D illustrate contraction measurement of target tissue in response to an ablation procedure in accordance with some embodiments.

DETAILED DESCRIPTION

Figure 1:
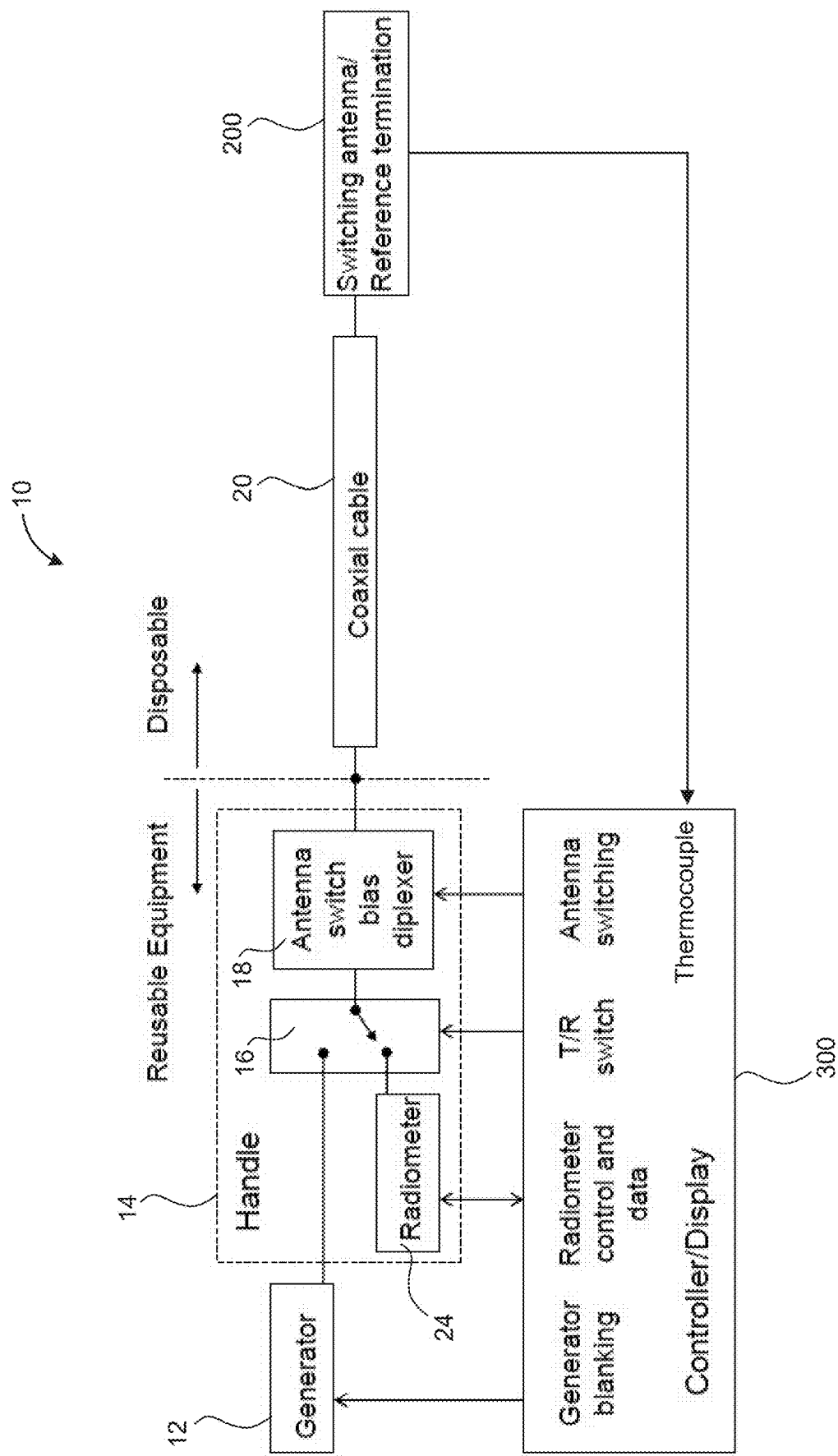
FIG. 1 is a block diagram of an exemplary microwave ablation system.

This technology relates to systems and methods for predicting the dimensions and location of a volume of ablated tissue in real-time during an ablation procedure based on radiometric signals indicative of the temperature of the tissue being ablated, as well as anatomical information. This technology also relates to non-destructive application of energy via a catheter to determine tissue type, which is useful during, or in preparation for, an ablation procedure. The ablation volume prediction algorithms described herein may use as an input radiometric signals received from a microwave ablation/radiometry system having a radiometer antenna configured for both heating and temperature sensing, as described in U.S. Pat. Nos. 11,337,756 and 12,064, 174 to Allison, the entire contents of each of which are incorporated herein by reference. For example, the microwave heating may be directed toward the target tissue, and a radiometer operating at the same time sharing the antenna with the microwave generator, may sense/monitor the microwave emissions from the region surrounding the antenna and convert these to tissue temperature. In this case, the target tissue being monitored includes, e.g., tumorous lung tissue. An algorithm computes the volume temperature reading based on the calculated tissue temperature at the target region. Microwave heating to target tissue and microwave radiometry as a means of monitoring the temperature of the heated tissue ensures that the desired temperatures are obtained to adequately treat the target tissue and achieve therapeutic goals.

Moreover, to avoid inaccurate radiometric temperature measurements that include the temperature of the coaxial cable due to dissipative loss in the cable running the length of the catheter, which may be indistinguishable from the emissions received by the antenna, the Dicke switch and reference termination, e.g., an internal reference input, are positioned at the end of the coaxial cable near the connection to the radiometer antenna such that the coaxial cable is part of both the target measurement from the radiometer antenna and the reference measurement from the reference termination, and heat dissipating therefrom drops out of the temperature calculation. Unlike standard thermocouple techniques used in existing commercial ablation systems, a radiometer may provide useful information about tissue temperature at depth—where the tissue ablation occurs—and thus provide feedback to the clinician about the extent of tissue damage as the clinician ablates a selected region of the target tissue.

Specifically, the present disclosure overcomes the drawbacks of previously-known systems by providing improved systems and methods for monitoring growth of the volume of ablation of target tissue during an ablation procedure, e.g., by displaying a predicted volume of ablated tissue overlaid on a medical image depicting the target tissue in real-time. Moreover, the present disclosure provides improved systems and methods for analyzing the radiometric signals to determine various properties of the tissue being ablated, e.g., tissue type or water content, as well as physical properties of surrounding tissue, and for adapting ablation volume prediction to account for surface boundaries and contours of the target tissue, and adjacent anatomical structures such as, e.g., airways, blood vessels, bile ducts, etc. The novel inventions described herein may have application to catheter/probe-based therapies, including but not limited to targets in the vascular system and soft tissue targets in liver, kidney, prostate, and lung. For example, the principles of the present disclosure described herein may be incorporated into known robotic surgical systems such as Galaxy System™ (available by Noah Medical, San Carlos, California) for navigated procedures.

Referring now to FIG. 1, an exemplary microwave heating and temperature sensing system is provided. As shown in FIG. 1, system 10 may include generator 12, handle 14 having Transmit/Receive (T/R) switch 16, antenna switch bias diplexer 18, and radiometer 24, and controller 300 operatively coupled to generator 12 and the electronic components of handle 14. In addition, system 10 may include a radiometer antenna, e.g., switching antenna 200, and cable 20, e.g., a coaxial cable, for electrically coupling switching antenna 200 to handle 14, and accordingly, generator 12 and controller 300. As shown in FIG. 1, generator 12 may supply ablative energy to switching antenna 200 through T/R switch 16 followed by antenna switch bias diplexer 18. Generator 12 may be any previously-known commercially available ablation energy generator, e.g., a microwave energy generator, thereby enabling radiometric techniques to be employed with reduced capital outlay. As will be readily understood to one skilled in the art, while FIG. 1 is illustrated to show one controller, controller 300 may include multiple processors utilized in a single location/housing or multiple locations/housings. Further, the reusable equipment in FIG. 1 may be housed in a common housing or separate housings.

Further, radiometer 24 is configured to receive temperature measurements from switching antenna 200 via cable 20. Switching antenna 200 includes a main antenna having one or more microwave radiating elements for emitting microwave energy and for measuring temperature of tissue adjacent the main antenna, and a reference termination for measuring a reference temperature. In addition, switching antenna 200 includes a switching network, e.g., a Dicke switch, integrated therein for detecting the volumetric temperature of tissue subjected to ablation. The switching network selects between the signals indicative of measured radiometer temperature from the main antenna of switching antenna 200, e.g., the temperature of the tissue adjacent the main antenna during the ablation procedure, and signals indicative of the measured reference temperature from the reference termination of switching antenna 200.

T/R switch 16 and antenna switch bias diplexer 18 may be disposed within handle 14, along with radiometer 24 for receiving temperature measurements from switching antenna 200 depending on the state of T/R switch 16. For example, T/R switch 16 may be in an ablation state such that microwave power may be transmitted from generator 12 to switching antenna 200, or T/R switch 16 may be in a measurement state such that radiometer 24 may receive temperature measurement from switching antenna 200, e.g., from the main antenna and/or the reference termination. Accordingly, switch bias diplexer 18 may be in a main antenna state such that radiometer 24 may receive temperature measurement from the main antenna, or switch bias diplexer 18 may be in a reference termination state such that radiometer 24 may receive temperature measurement from the reference termination. Handle 14 may be reusable, while cable 20 and switching antenna 22 may be disposable. In some embodiments, at least one of the switching components, e.g., T/R switch 16 and switch bias diplexer 18, may be integrated in switching antenna 200.

The microwave power propagates from generator 12 down cable 20 in the catheter to switching antenna 200 at the catheter tip. The microwave power radiates outward from the main antenna of switching antenna 200 into the target tissue, e.g., target lung tissue such as a tumor. The volume of blood flowing through the body lumen at body temperature may cool the surface of the body lumen in immediate contact with the blood. In addition to, or alternatively, coolant from outside the body, introduced through a coolant lumen of the catheter may be used to cool the surface of the body lumen, as described in U.S. Pat. No. 12,064,174. Tissue beyond the lumen wall that does not experience this cooling will heat up. Sufficient microwave power may be supplied to heat the target tissue, e.g., nerve area, to a temperature that destroys the target tissue. In addition, controller 300 may be operatively coupled to one or more thermocouples configured to measure a reference temperature, and optionally, the temperature of tissue surrounding switching antenna 200 during an ablation procedure, as described in further detail below. Accordingly, controller 300 may directly receive voltages returned by the thermocouple, as shown in FIG. 1, wherein the received voltages are indicative of the reference and/or tissue temperatures measured by the thermocouple.

Figure 2A:
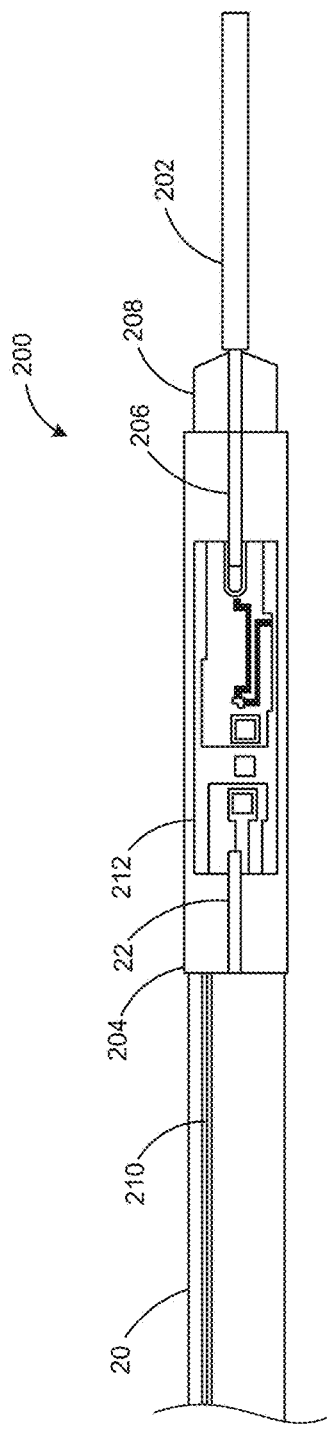
FIG. 2A illustrates an exemplary radiometer antenna of the microwave ablation system of FIG. 1.
Figure 2B:
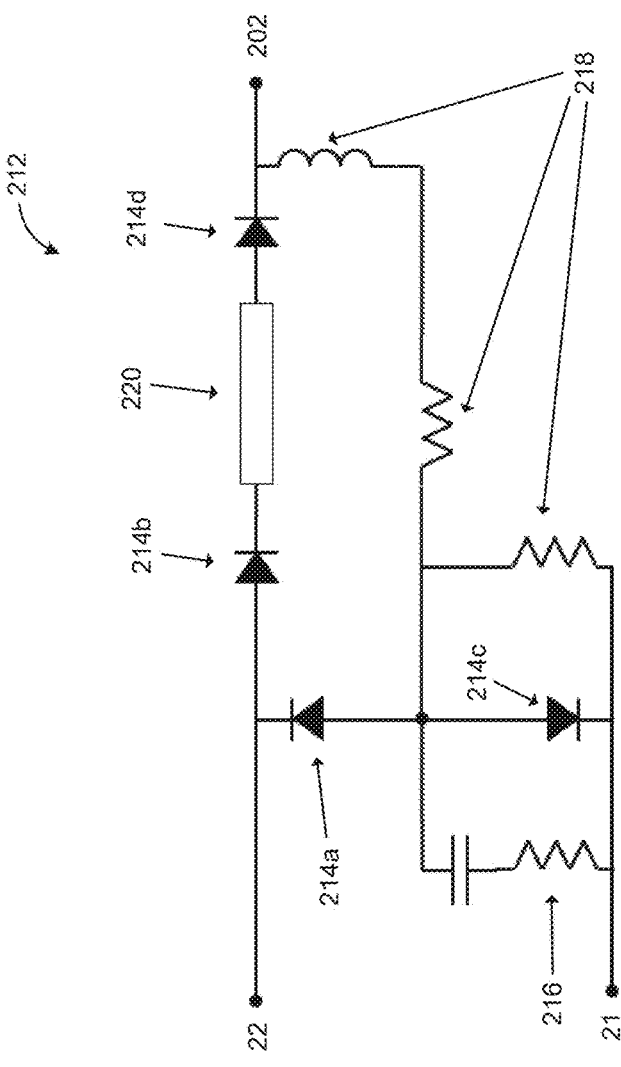
FIG. 2B illustrates an exemplary switching network of the radiometer antenna of FIG. 2A.

Referring now to FIGS. 2A and 2B, an exemplary switching antenna is provided. As shown in FIG. 2A, switching antenna 200 may include main antenna 202 extending distally from and electrically coupled to switching network 212, e.g., a Dicke switch, disposed within substrate carrier 204. For example, main antenna 202 may be electrically coupled to switching network 212 via inner conductor 206, and spacer 208, e.g., a polycarbonate spacer, may be positioned within the distal region of substrate carrier 204 and around inner conductor 206. Moreover, the distal end of cable 20, e.g., a coaxial cable, may be coupled to the proximal end of substrate carrier 204 such that cable 20 may be electrically coupled to switching network 212, and accordingly main antenna 202, via inner conductor 22. As shown in FIG. 2A, one or more thermocouples 210 may be electrically coupled to cable 20, e.g., at the junction of cable 20 and substrate carrier 204. For example, the free end of thermocouple 210 may be disposed within the coolant lumen in fluid communication with the coolant used to cool the surface of the body lumen, as described above. Accordingly, thermocouple 210 may be configured to measure a reference temperature and return a voltage value indicative of the measured reference temperature, which may be converted to the reference temperature at the location of thermocouple 210, e.g., by controller 300. For example, the voltage value returned by thermocouple 210 may be well above any noise level, e.g., around 100 mV.

Additionally, or alternatively, the free end of the same or another thermocouple 210 may extend along at least a portion of the outer surface of switching antenna 200, e.g., the outer surface of main antenna 202, such that the free end of thermocouple 210 is in direct contact with tissue surrounding switching antenna 200 as energy is emitted by main antenna 202 during an ablation procedure. Accordingly, thermocouple 210 may be configured to measure the temperature of the tissue surrounding the antenna during an ablation procedure and similarly return a voltage value indicative of the measured tissue temperature, which may be converted to the tissue temperature at the location of thermocouple 210, e.g., by controller 300.

Main antenna 202 may be configured to emit energy, e.g., microwave energy, supplied by generator 12, e.g., when T/R switch 16 is in the ablation state. In addition, main antenna 202 may be configured to measure radiometer temperature, e.g., temperature of tissue adjacent main antenna 202, when T/R switch 16 is in the measurement state. For example, main antenna 202 may include means for detecting microwave emissions from the region surrounding the antenna, e.g., thermal noise, and may convert these to temperature of the tissue adjacent switching antenna 200, i.e., radiometer temperature. As shown in FIG. 2B, switching antenna 200 may include reference termination 216 for measuring a reference temperature, e.g., when T/R switch 16 is in the measurement state, as well as first switching diode 214a, second switching diode 214b, and third switching diode 214c, and fourth switching diode 214d, as described in U.S. Pat. No. 12,064,174. For example, reference termination 216 may detect microwave emissions from the region surrounding reference termination 216, e.g., thermal noise, and may convert these to the reference temperature at the location of reference termination 216. Accordingly, the volume temperature output $T_{tissue}$ will be the sum of the difference between the radiometer temperature $T_{tissue\_rad}$, e.g., the, and the reference temperature $T_{ref\_rad}$ measured by reference termination 216, and the reference temperature $T_{ref\_thermo}$ measured by thermocouple 210, as illustrated in the equation below.

$$T_{tissue\_rad} - T_{ref\_rad} + T_{ref\_thermo} = T_{tissue}$$

Alternatively, in some embodiments, the volume temperature output $T_{tissue}$ may be $T_{tissue\_thermo}$ measured by thermocouple 210 as illustrated in the equation below. Accordingly, the voltage returned by thermocouple 210 indicative of the tissue temperatures may be directly received by controller 300 for processing.

$$T_{tissue\_thermo} = T_{tissue}$$

Switching diodes 214a, 214b, 214c, 214d may be, e.g., microwave PIN diodes, and may be biased with a small forward current in the ON state or back biased with a negative voltage in the OFF state. Input from main antenna 202 or from reference termination 216 may be selected by reversing the polarity of the bias current applied to inner conductor 22 of cable 20. Resistors, e.g., bias components 218, return the bias current through outer conductor 21 of cable 20. A bias current diplexer may supply the bias to the proximal end of the catheter outside the body. Third switching diode 214c may improve isolation of reference termination 216 from the radiometer temperature, e.g., heating of tissue due to ablation, during ablation of the target tissue. Fourth switching diode 214d may improve isolation of reference termination 216 from the radiometer temperature during measurement of the reference temperature. As shown in FIG. 2B, fourth switching diode 214d and second switching diode 214b may be in series with main antenna 202, and separated by microstrip transmission line 220 on the switching network substrate. Microstrip transmission line 220 may improve the isolation achieved by the two switching diodes 214b, 214d, which may be especially useful for applications using higher ablation frequencies.

Figure 3:
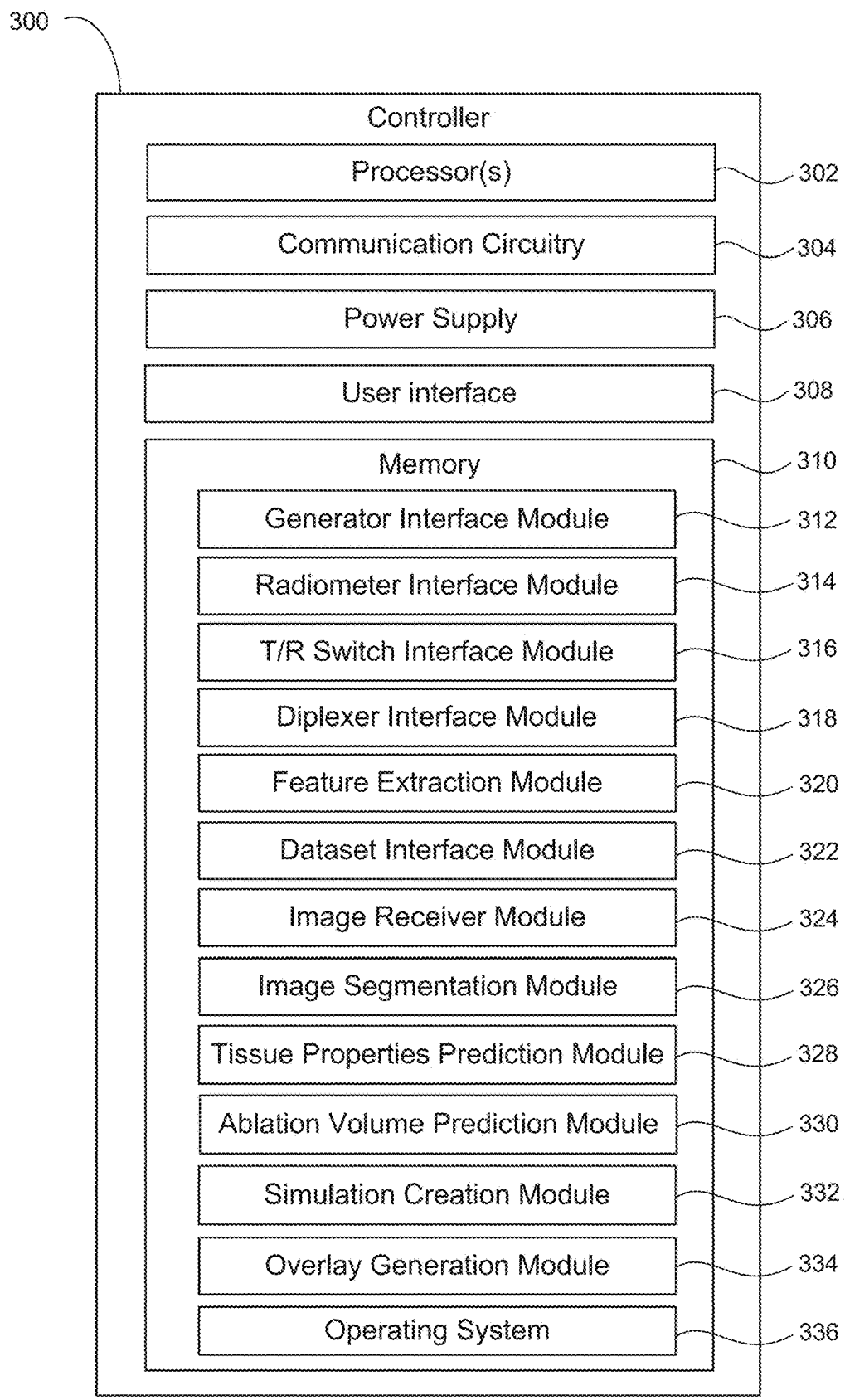
FIG. 3 shows some example components that may be included in the controller of the microwave ablation system of FIG. 1 in accordance with some embodiments.

Referring now to FIG. 3, some example components that may be included in controller 300 are provided. As described above, controller 300 may be operatively coupled to generator 12 and switching antenna 200 via, e.g., handle 14 and cable 20, to coordinate signals therebetween. Controller 300 thereby provides generator 12 with the information required for operation, transmits ablative energy to switching antenna 200 under the control of the clinician, and may display the temperature at depth of tissue as it is being ablated as well as a graphical representation of the shape and location of predicted volume of ablated tissue in real-time, for use by the clinician. The displayed temperature and predicted ablation volume may be calculated based on signal(s) measured by switching antenna 200 using computer algorithms, as described in further detail below.

As shown in FIG. 3, controller 300 may include one or more processors 302, communication circuitry 304, power supply 306, user interface 308, and/or memory 310 for storing instructions to be executed by controller 300. One or more electrical components and/or circuits may perform some of or all the roles of the various components described herein. Although described separately, it is to be appreciated that electrical components need not be separate structural elements. For example, processor 302 and communication circuitry 304 may be embodied in a single chip. In addition, while controller 300 is described as having memory 310, a memory chip(s) may be separately provided. Controller 300, in conjunction with firmware/software stored in the memory may execute an operating system (e.g., operating system 336), such as, for example, Windows, Mac OS, Unix or Solaris 5.10. Controller 300 also executes software applications stored in the memory. For example, the software may be programs in any suitable programming language known to those skilled in the art, including, for example, C++, PHP, or Java.

Processor 302 may comprise one or more commercially available microcontroller units that may include a programmable microprocessor, volatile memory, nonvolatile memory such as EEPROM for storing programming, and nonvolatile storage, e.g., Flash memory, for storing firmware. Processor 302 may consist of one or more processors and may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. Controller 300 also may be implemented as a combination of computing devices, e.g., a combination of a DSP and a microprocessor, a plurality of microprocessors, one or more microprocessors in conjunction with a DSP core, or any other such configuration. Processor 302 is configured to be programmable such that programming data is stored in the memory of the processor or accessible via a network.

Communication circuitry 304 may include circuitry that allows controller 300 to communicate with an image capture device and/or other computing devices for receiving image files, e.g., medical images such as a CT scan image, a CBCT scan image, a tomosynthesis image based on X-ray, an MRI image, and/or an echographic B-mode image. Additionally, or alternatively, image files may be directly uploaded to controller 300. Communication circuitry 304 may be configured for wired and/or wireless communication over a network such as the Internet, a telephone network, a Bluetooth network, and/or a WiFi network using techniques known in the art. Communication circuitry 304 may be a communication chip known in the art such as a Bluetooth chip and/or a WiFi chip. Communication circuitry 304 permits controller 300 to transfer information, such temperature measurements and predicted ablation volume data, locally and/or to a remote location such as a server.

Power supply 306 may supply alternating current or direct current. In direct current embodiments, power supply may include a suitable battery such as a replaceable battery or rechargeable battery and apparatus may include circuitry for charging the rechargeable battery, and a detachable power cord. Power supply 306 may be charged by a charger via an inductive coil within the charger and inductive coil. Alternatively, power supply 306 may be a port to allow controller 300 to be plugged into a conventional wall socket, e.g., via a cord with an AC to DC power converter and/or a USB port, for powering components within controller 300.

User interface 308 may be used to receive inputs from, and/or provide outputs to, a user. For example, user interface 308 may include a touchscreen, display, switches, dials, lights, etc. Accordingly, user interface 308 may display information such as temperature measurement data, ablation power level and/or duration, medical images overlaid with predicted ablation volume, etc. to provide useful feedback to a user during an ablation procedure, as described in further detail below. Moreover, user interface 308 may receive user input including, for example, manual labeling of a lesion on a pre-operative medical image. In some embodiments, user interface 308 is not present on controller 300, but is instead provided on a remote, external computing device communicatively connected to controller 300 via communication circuitry 304.

Controller 300 may contain memory and/or be coupled, via one or more buses, to read information from, or write information to, memory. Memory 310 may include processor cache, including a multi-level hierarchical cache in which different levels have different capacities and access speeds. Memory 310 may also include random access memory (RAM), other volatile storage devices, or non-volatile storage devices. Memory 310 may be RAM, ROM, Flash, EEPROM, other volatile storage devices or non-volatile storage devices, or other known memory, or some combination thereof, and preferably includes storage in which data may be selectively saved. For example, the storage devices can include, e.g., hard drives, optical discs, flash memory, and Zip drives. Memory 310 stores program instructions that, when executed by processor 302, cause processor 302 and the functional components of system 10 to provide the functionality ascribed to them herein. For example, programmable instructions may be stored on memory 310 to execute algorithms for calculating target tissue temperature, predicting volume of ablation of target tissue, and determining target tissue properties such as, e.g., tissue type.

Memory 310, which is one example of a non-transitory computer-readable medium, may be used to store operating system (OS) 336, generator interface module 312, radiometer interface module 314, T/R switch interface module 316, diplexer interface module 318, feature extraction module 320, dataset interface module 322, image receiver module 324, image segmentation module 326, tissue properties prediction module 328, ablation volume prediction module 330, simulation creation module 332, and overlay generation module 334. The modules are provided in the form of computer-executable instructions that may be executed by processor 302 for performing various operations in accordance with the disclosure.

Generator interface module 312 may be executed by processor 302 for causing generator 12 to supply energy, e.g., microwave energy, to the main antenna of switching antenna 200 via cable 20 for emission to target tissue, e.g., when T/R switch 16 is in the ablation state. Generator interface module 312 further may modulate the level of energy emitted via the main antenna of switching antenna 200 based on the calculated volumetric temperature of the tissue subject to ablation continuously as part of a feedback loop to ensure that the temperature of the target tissue is maintained within a predetermined threshold.

Radiometer interface module 314 may be executed by processor 302 for causing radiometer 24 to receive radiometric signals indicative of temperature measurement from switching antenna 200, e.g., from the main antenna and/or the reference termination, when T/R switch 16 is in the measurement state, and for receiving the radiometric signals from radiometer 24. For example, radiometer interface module 314 may receive signals indicative of measured radiometer temperature from the main antenna of switching antenna 200, e.g., the temperature of the tissue adjacent switching antenna 200 during the ablation procedure, when switch bias diplexer 18 is in the main antenna state, and signals indicative of the measured reference temperature from the reference termination of switching antenna 200 when switch bias diplexer 18 is in the reference termination state. Accordingly, the processor may calculate the volumetric temperature of the tissue subject to ablation based on the signals as described in U.S. Pat. No. 12,064,174.

Moreover, radiometer interface module 314 initially may filter the radiometric signals upon receipt from radiometer 24. For example, radiometer interface module 314 may use anti-spike filtering on the radiometric signal to remove one or more incorrect points within the radiometric signal, as well as smoothing filtering on the radiometric signal to generate a smoother signal. For anti-spike filtering, radiometer interface module 314 may use either a moving minimum or an algorithm based on a first derivative. For smoothing filtering, radiometer interface module 314 may use a Kalman filter, a moving average, or fitting the radiometric signal to a function of the form:

$$\frac{a*x^3 + b*x^2 + c*x + d}{e*x^3 + f*x^2 + g*x + 1}$$

As described above, controller 300 further may receive voltage returned by thermocouple 210 indicative of the temperature of tissue and/or the reference temperature measured by thermocouple 210 at switching antenna 200. Accordingly, controller 300 further may include a thermocouple interface module (not shown) that may be executed by processor 302 for receiving the voltages returned by thermocouple 210, and converting these voltages to temperature values.

T/R switch interface module 316 may be executed by processor 302 for directing T/R switch 16 to transition between the ablation state and the measurement state as described above. For example, in some embodiments, T/R switch interface module 316 may direct T/R switch 16 to be positioned in the ablation state for a majority of an ablation period, e.g., more than 50%, more than 75%, more than 80%, or preferably more than 90%, to maximize the power dissipated. Accordingly, T/R switch interface module 316 may direct T/R switch 16 to be positioned in the measurement state for the remainder of the ablation period, e.g., less than 50%, less than 25%, less than 20%, or preferably less than 10%, respectively.

Diplexer interface module 318 may be executed by processor 302 for directing switch bias diplexer 18 to transition between the main antenna state and the reference termination state as described above. For example, during the ablation period when T/R switch 16 is in the measurement state, diplexer interface module 318 may direct switch bias diplexer 18 to alternate between being positioned in the main antenna state and the reference termination state. For example, in a one second cycle, T/R switch interface module 316 may direct T/R switch 16 to be positioned in the ablation state for 900 milliseconds such that the main antenna emits microwave energy to the target tissue for 900 milliseconds, and then direct T/R switch 16 to be positioned in the measurement state for 100 milliseconds. During the 100 milliseconds that T/R switch 16 is in the measurement state, diplexer interface module 318 may direct switch bias diplexer 18 to alternate between the main antenna state and the reference termination state every, e.g., 1, 2, 3, 4, or 5 milliseconds. As will be understood by a person having ordinary skill in the art, T/R switch interface module 316 may direct T/R switch 16 to be positioned in the ablation state for more or less than 900 milliseconds, and diplexer interface module 318 may direct switch bias diplexer 18 to alternate every time period that include any time less than 1 millisecond or more than 5 milliseconds.

Feature extraction module 320 may be executed by processor 302 for processing and analyzing the radiometric signals received by radiometer interface module 314 from radiometer 24, e.g., the radiometric signals filtered by radiometer interface module 314, to extract one or more features of the radiometric signal including, for example, the area under the temperature curve, a maximum tissue temperature, a thermal dose of the tissue temperature, an initial slope of the tissue temperature, and/or an average rise of the tissue temperature. For example, to compute the thermal dose, feature extraction module 320 may first compute CEM 43, i.e., cumulative equivalent minutes at 43° C., and then take the logarithm of CEM 43. CEM 43 may be computed using the formula:

$$CEM43 = \int_0^t R^{43-T} dt$$

where T is the temperature; t is the time; and R is ¼ if T is less than or equal to 43, or ½ if T is larger than 43.

Moreover, feature extraction module 320 may determine the initial slope of the tissue temperature from the initial rise in tissue temperature responsive to energy emission by the main antenna of switching antenna 200 over an initial predetermined time period, e.g., within 2 to 15 seconds of energy emission to the target tissue, or preferably 3 seconds. Additionally, or alternatively, feature extraction module 320 may be executed by processor 302 for processing and analyzing the temperature measurements obtained by thermocouple 210, rather than the radiometric signals received by radiometer interface module 314 from radiometer 24, to thereby extract the one or more features of the thermocouple temperature measurements, as described above, e.g., the area under the temperature curve, a maximum tissue temperature, a thermal dose of the tissue temperature, an initial slope of the tissue temperature, and/or an average rise of the tissue temperature.

Dataset interface module 322 may be executed by processor 302 for accessing one or more datasets stored in memory 310, or stored remotely via communication circuitry 304. The datasets may include data resulting from previous experiments and/or simulations. For example, a dataset may include a plurality of actual ablation volumes for given thermal dose values and/or short axis values obtained from previous experiments and/or simulations, as well as a trend line based on the actual ablation volumes and thermal dose/short axis values, and/or initial slopes and corresponding electromagnetic properties of target tissue, as described in further detail below. In addition, the dataset further may include information indicative of temperatures of tissues surrounding an antenna resulting from energy emission thereto by the antenna, e.g., radiometric signal values and/or thermocouple temperature measurements, from previous experiments and/or simulations, as well as associated average tissue property values, e.g., relative permittivity of the tissue, electrical conductivity, thermal capacity, etc., for various tissue types.

Image receiver module 324 may be executed by processor 302 for receiving medical images including, for example, CT scan images, CBCT scan images, tomosynthesis images based on X-ray, MRI images, and/or echographic B-mode images. For example, image receiver module 324 may receive pre-operative images of the target tissue within a patient, e.g., a "pre-CT" image, which may include anatomical structures within/adjacent to the target tissue such as airways, blood vessels, etc. The pre-operative images may be pre-labeled, e.g., labeled prior to receipt by image receiver module 324, or may be labeled, either manually by a user or automatically, to indicate an area of interest, e.g., a lesion such as cancerous tissue to be ablated. For example, the pre-operative images may be labeled by a user via user interface 308 upon receipt by image receiver module 324. Additionally, or alternatively, the pre-operative images may be automatically labeled via automated segmentation algorithms, as described in further detail below.

Pre-operative images of the target tissue without the antenna in place may be of higher quality and easier to label the area(s) of interest. In addition, image receiver module 324 may receive medical images of the target tissue taken during the ablation procedure that include the main antenna of switching antenna 200, e.g., a "per-CT" image. Image receiver module 324 further may receive pre-operative and post-operative images of target tissue before and after an ablation procedure, e.g., from previous ablation procedures, which may be used to determine physiological effects on the target tissue resulting from the ablation, e.g., contraction of the target tissue, as described in further detail below. As will be understood by a person having ordinary skill in the art, while "pre-CT" and "per-CT" references pre-operative CT images and CT images taken during the ablation procedure, e.g., including the antenna, respectively, the medical images may include medical images other than CT images as described above.

Image segmentation module 326 may be executed by processor 302 for automatically segmenting the medical images received by image receiver module 324, e.g., pre-CT and per-CT images, to thereby classify one or more components and/or anatomical structures in the medical images. For example, image segmentation module 326 may segment and label the target tissue, e.g., the target organ, on both the pre-CT image and the per-CT image. As described above, pre-operative images of the target tissue without the antenna in place may be of higher quality and easier to label the area(s) of interest, and thus, image segmentation module 326 preferably may execute a segmentation algorithm to segment and label the antenna only in the per-CT image, e.g., using method 400 shown in FIG. 4.

Figure 4:
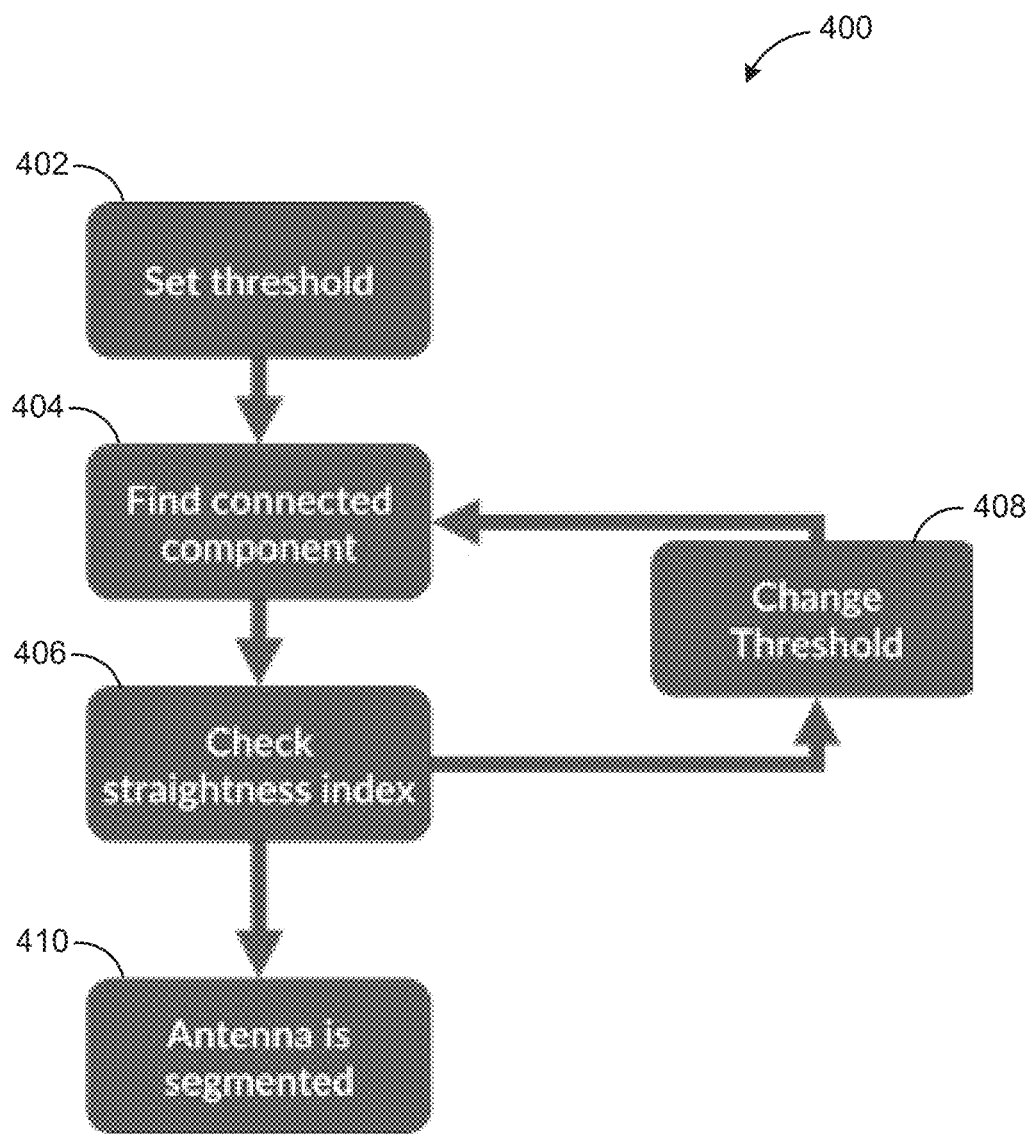
FIG. 4 is a flow chart illustrating exemplary method steps for segmenting a radiometer antenna in medical images in accordance with some embodiments.

As shown in FIG. 4, at step 402, the segmentation algorithm may threshold the medical image with an adaptive threshold based on the medical image. For example, the threshold may be the 99th percentile of the pixel value. The resulting thresholded medical image may be a black and white image. At step 404, the segmentation algorithm may compute one or more connected components of the thresholded medical image, e.g., the areas in white that are connected together, and discard any of the connected components smaller than a predetermined size, e.g., less than 1000 voxels. Accordingly, the remaining connected components may all be larger than the predetermined size. At step 406, the segmentation algorithm may compute a straightness index for each of the remaining connected components. For example, for each of the remaining connected components, the segmentation algorithm may select three random points on the connected component, calculate an angle between the three random points, and determine a value based on a minimum of an extra-angle and the angle. The segmentation algorithm may repeat these steps a plurality of times, e.g., 200 times, each time resulting in a respective value. As will be understood by a person having ordinary skill in the art, the steps may be repeated less or more than 200 times.

Next, the segmentation algorithm may compute a straightness index for each of the connected components as an average of the respective determined values. The segmentation algorithm may compare the straightness index of each remaining connected component against a predetermined threshold, e.g., 0.4. If none of the straightness indexes are below the predetermined threshold, at step 408, the segmentation algorithm may change the adaptive threshold, and return to step 404 to compute one or more connected components of the medical image thresholded with the new adaptive threshold. If at least one of the straightness indexes are below the predetermined threshold at step 406, at step 410, the segmentation algorithm may classify the connected component with the lowest straightness index as the antenna. In addition, the segmentation algorithm may label the antenna on the per-CT image. Upon segmentation of the antenna, the per-CT image may be realigned in the axis of the antenna to provide a better view of the ablation zone.

Referring again to FIG. 3, image segmentation module 326 further may segment and label one or more anatomical structures present in the medical images including, for example, an airway, a blood vessel, bile ducts, etc., which also may be overlaid on the overlaid per-CT image, as described in further detail below. Moreover, image segmentation module 326 may compute the surface boundaries and contours of the segmented components and anatomical structures.

Tissue properties prediction module 328 may be executed by processor 302 for determining one or more properties of the target tissue, e.g., tissue type, based on the received tissue temperature information, e.g., radiometric signals received from radiometer 24 and/or temperature measurements received from thermocouple 210. For example, tissue properties prediction module 328 may determine which organ switching antenna 200 is disposed within. Specifically, different tissues may have different electromagnetic properties including, for example, relative permittivity of the tissue ($\varepsilon$), electrical conductivity ($\sigma$), thermal capacity (C), etc., which may cause the respective tissues to have different initial slopes responsive to energy emission thereto. For example, the liver and the lung may have different values of the combination of properties. Moreover, cancerous tissue may have different electromagnetic property combinations than healthy tissue.

Figure 5A:
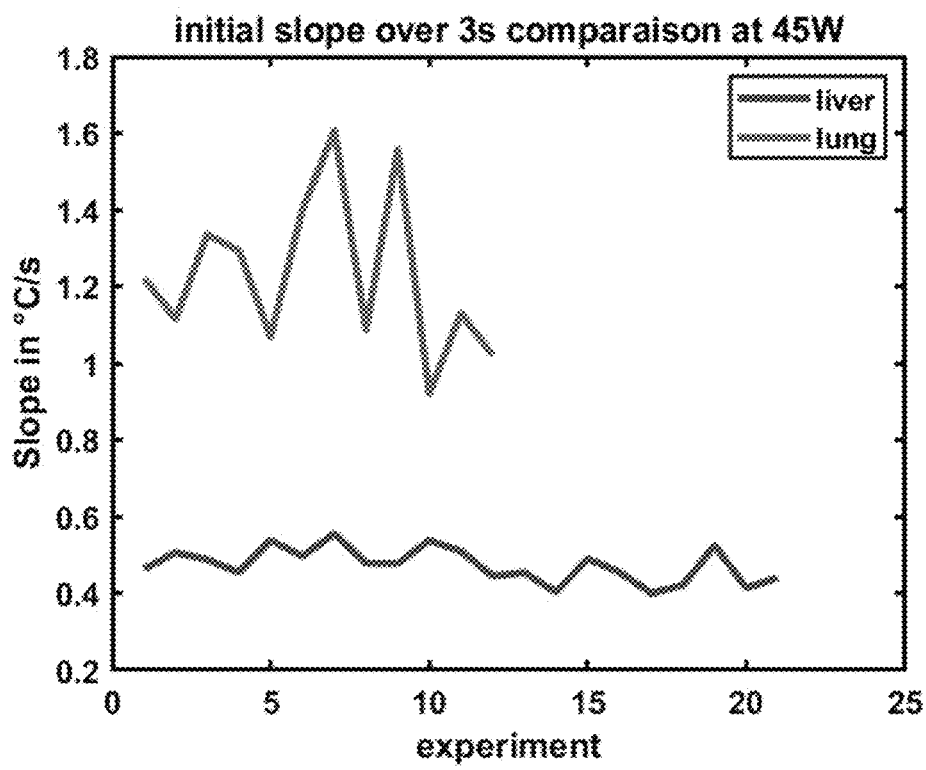
FIG. 5A is a graph illustrating initial slopes of temperatures of various target tissue types.

Accordingly, tissue properties prediction module 328 may determine the type of tissue being ablated based on the initial slope extracted from the radiometric signals by feature extraction module 320, as well as information from the datasets accessed by dataset interface module 322. For example, tissue properties prediction module 328 may compare the initial slope extracted from the radiometric signal with a dataset of initial slope values obtained from previous experiments/simulations to detect electromagnetic properties of the target tissue, and determine the type of target tissue. As shown in FIG. 5A, for a computed initial slope within 1-1.6° C./s at a power level of 45 W, based on previous experimental data, tissue properties prediction module 328 may determine that the target tissue is lung tissue, and for a computed initial slope within 0.4-0.6° C./s at a power level of 45 W, based on previous experimental data, tissue properties prediction module 328 may determine that the target tissue is liver tissue. Tissue properties prediction module 328 similarly may determine the type of tissue being ablated based on the initial slope extracted from the temperature measurements provided by thermocouple 210.

Figure 5B:
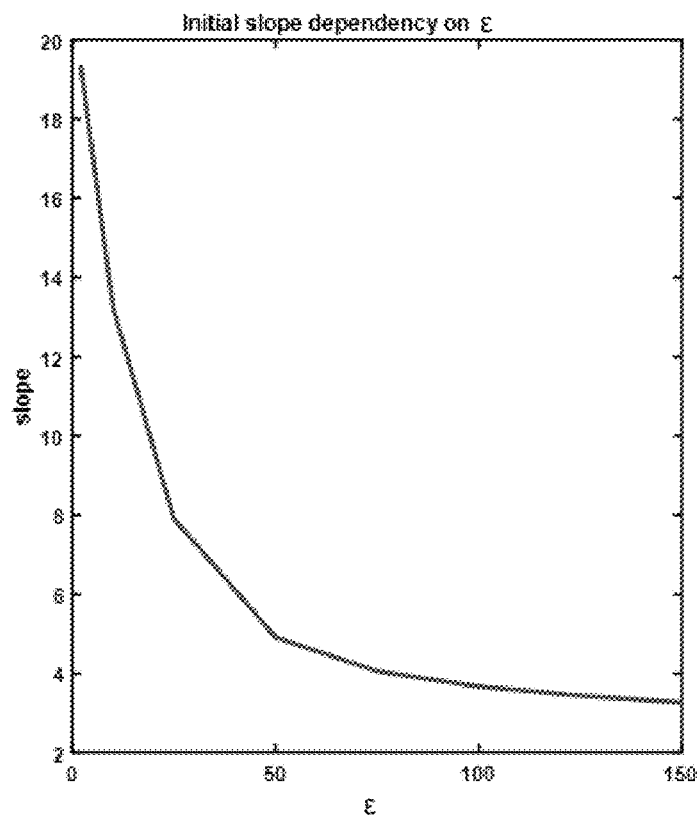
FIG. 5B is a graph illustrating changes of initial slopes of radiometric signals with respect to changes in relative permittivity of the tissue.

In addition, as described above, the temperature of tissue heated during an ablation procedure, e.g., radiometric temperature/thermocouple tissue temperature, for a given patient during an ablation procedure may depend on patient specific tissue properties. For example, as shown in FIG. 5B, which illustrates the variation of the initial slope values extracted from radiometric signals with respect to the relative permittivity of the tissue ($\varepsilon$), variations in tissue property parameters have a direct impact on the initial slope of the radiometric signal. Accordingly, tissue properties prediction module 328 further may estimate patient specific tissue property parameters, e.g., relative permittivity of the tissue ($\varepsilon$), electrical conductivity ($\sigma$) thermal capacity (C), etc., in real-time based on the radiometric signal measured during an ablation procedure in real-time and a dataset of radiometric signals obtained from previous experiments/simulations including associated average tissue property parameter values for the same tissue type. For example, tissue properties prediction module 328 may analyze the datasets to find correlations, e.g., datasets that include radiometric signals obtained from previous experiments/simulations that are the same as (or similar) to the real-time radiometric signal as well as corresponding average tissue property parameter values, and use the correlating dataset to estimate the patient specific tissue property parameter values. The patient specific tissue property parameters computed using the radiometric temperature may be an average of the properties of the tissue around the antenna.

Accordingly, based on the known type of target tissue and/or the patient specific tissue property parameters, the predicted ablation volume may be further adaptive to take in account the effect of the electromagnetic properties of the target tissue on the ablation volume, as described in further detail below. In some embodiments, tissue properties prediction module 328 similarly may estimate patient specific tissue property parameters, e.g., relative permittivity of the tissue ($\varepsilon$), electrical conductivity ($\sigma$), thermal capacity (C), etc., in real-time based on the tissue temperature measured by thermocouple 210 during an ablation procedure in real-time and a dataset of thermocouple tissue temperatures obtained from previous experiments/simulations including associated average tissue property parameter values for the same tissue type. In addition, tissue properties prediction module 328 further may compute tissue property parameter values of other anatomical structures, e.g., an airway, adjacent to antenna 200 based on the geometry of the other anatomical structures, e.g., obtained from image segmentation as described above, and the estimated patient specific tissue property parameters of the target tissue. The visibility of the tissue properties of the other anatomical structures in the radiometric signal/thermocouple temperature measurements will be greater the closer the anatomical structure is to antenna 200. Accordingly, the computed tissue property parameter values of the other anatomical structures may be used to adapt the patient specific simulation to simulate the behavior thereof during an ablation procedure.

Moreover, tissue properties prediction module 328 may determine the type of target tissue and/or the patient specific tissue property parameters based on radiometric signals/thermocouple temperature measurements obtained during non-destructive/minimally destructive emission of energy to the target tissue, e.g., energy emitted to the target tissue at a predetermined power level for a predetermined time period selected to avoid damaging/ablating the target tissue. Accordingly, generator interface module 312 may be executed by processor 302 for causing generator 12 to supply energy, e.g., microwave energy, to the main antenna of switching antenna 200 via cable 20 for emission to target tissue at the predetermined power level for the predetermined time period, e.g., when T/R switch 16 is in the ablation state. While the power level and duration of energy emission to the target tissue may be insufficient to damage/ablate the target tissue, they are sufficient to cause a rise in temperature of the target tissue, and accordingly, generate an initial slope of the target tissue. Moreover, monitoring the initial slope of the target tissue during the non-destructive/minimally destructive emission of energy to the target tissue may guide the clinician in positioning the antenna inside the target tissue. For example, changes in the initial slope while advancing the antenna may indicate changes in tissue, e.g., that the antenna is entering the lesion, thereby decreasing planning and positioning procedural time.

Figure 6A:
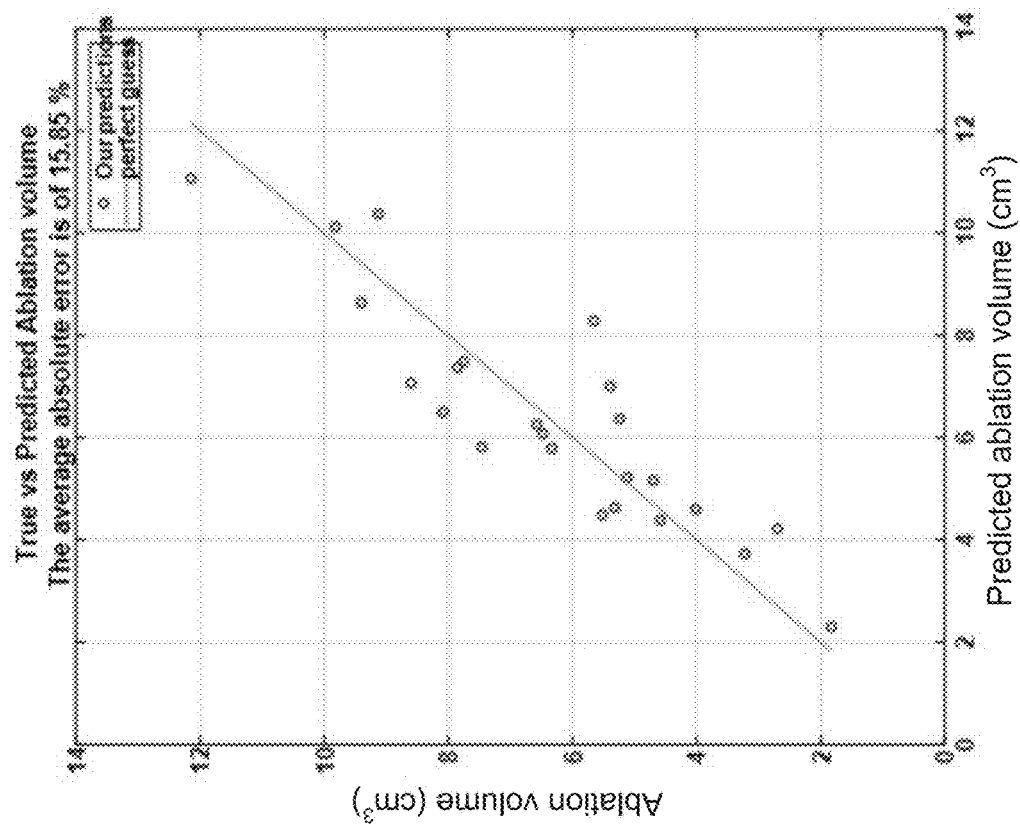
FIG. 6A illustrates trend lines for predicting ablation volume of target tissue based on thermal dose of radiometric temperature in accordance with some embodiments.
Figure 6A:
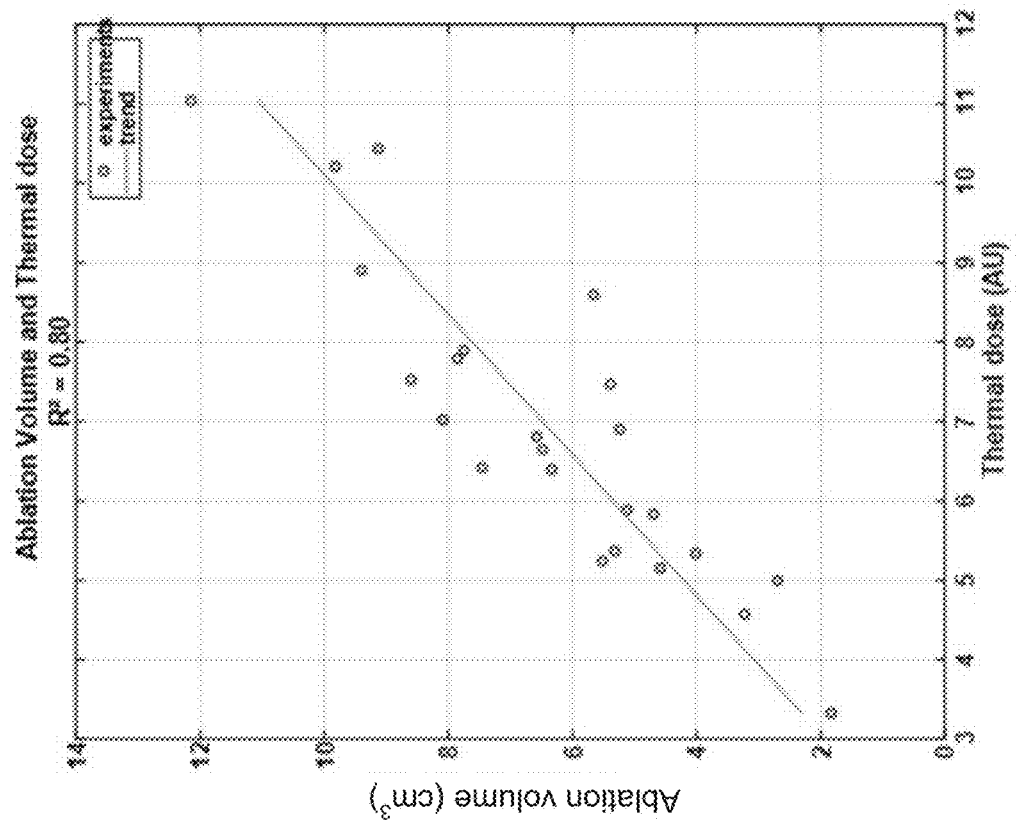
Figure 6B:
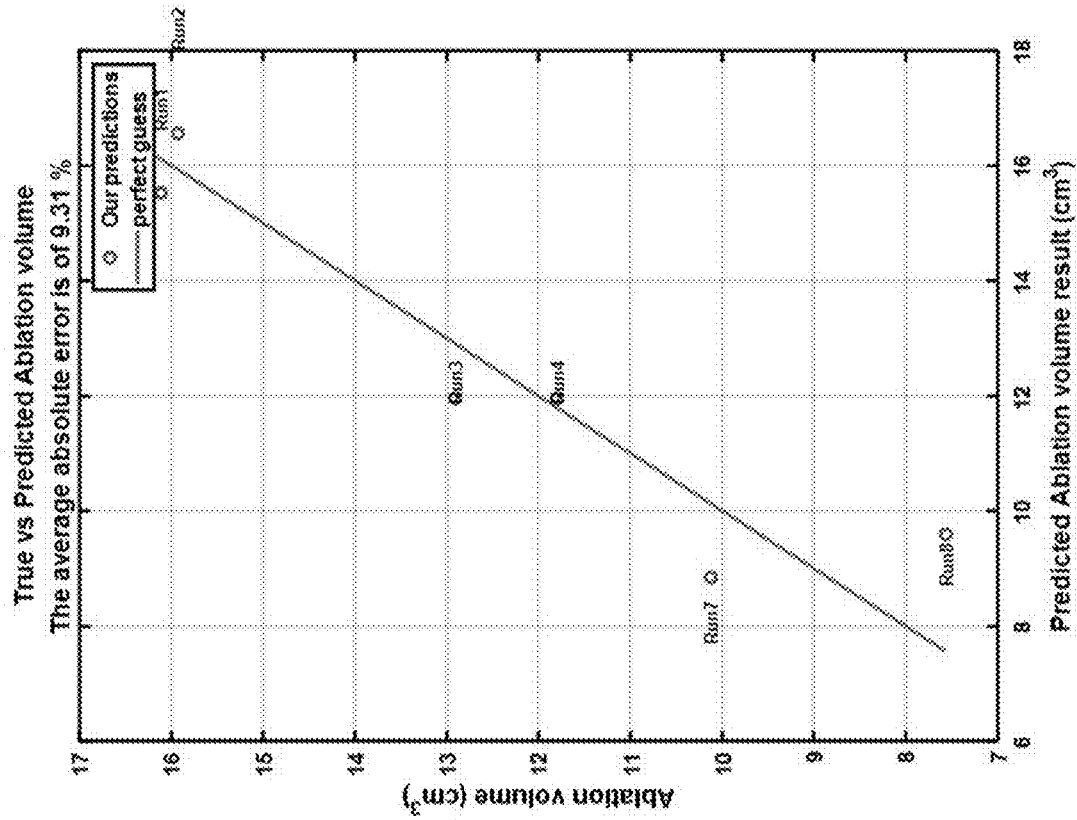
FIG. 6B illustrates trend lines for predicting ablation volume of target tissue based on maximum tissue temperature measured by a thermocouple in accordance with some embodiments.
Figure 6B:
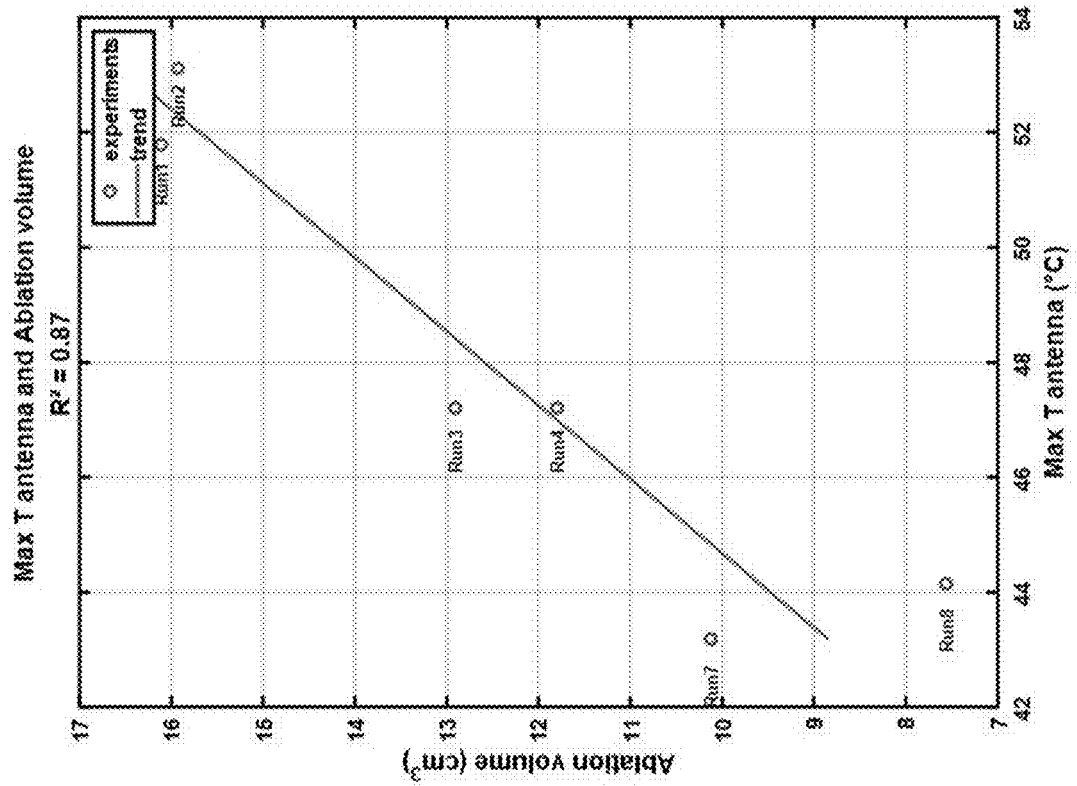

Ablation volume prediction module 330 may be executed by processor 302 for predicting a volume of ablated tissue during an ablation procedure responsive to energy emission to the target tissue, e.g., by the main antenna of switching antenna 200, based on the one or more features extracted from the radiometric signals/thermocouple temperature measurements by feature extraction module 320, as well as information from the datasets accessed by dataset interface module 322. For example, based on the computed thermal dose extracted from the radiometric signal, ablation volume prediction module 330 may analyze the datasets to find correlations, e.g., datasets that include the computed (or similar) thermal dose and corresponding ablation volumes, and use the correlating dataset to predict the ablation volume of the target tissue. As shown in FIG. 6A, for a computed thermal dose of 5 obtained from a radiometric signal, based on the trend line in the graph of ablation volume and thermal dose ($R^2$=0.80), ablation volume prediction module 330 may predict an ablation volume of 4.1 cm³. Additionally, ablation volume prediction module 330 further may predict the volume of ablation based at least on the power level of ablation energy. As shown in FIG. 6B, for a computed maximum tissue temperature (e.g., Max T antenna) of 47.2° obtained from a thermocouple temperature measurement, based on the trend line in the graph of ablation volume and thermal dose ($R^2$=0.87), ablation volume prediction module 330 may predict an ablation volume of 12 cm³. The data used to populate the "True vs Predicted Ablation volume" graph of FIG. 6B, is derived from experimental data depicted Table 1 copied below.

TABLE 1

| Run | Power (W) | Duration (min) | Depth (mm) | Volume (cm³) |
|---|---|---|---|---|
| 1 | 100 | 10 | 11 | 16.114 |
| 2 | 100 | 10 | 3 | 15.925 |
| 3 | 80 | 10 | 11 | 12.911 |
| 4 | 80 | 10 | 3 | 11.798 |
| 7 | 80 | 5 | 11 | 10.128 |
| 8 | 80 | 5 | 3 | 7.565 |

Figure 7A:
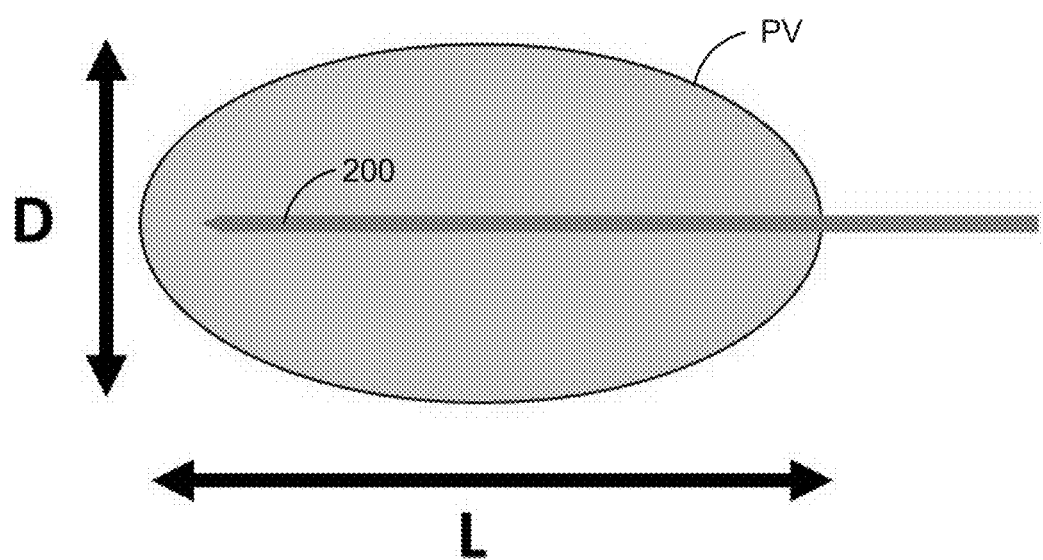
FIG. 7A illustrates exemplary dimensions of a predicted ablation volume of target tissue relative to a radiometer antenna.
Figure 7B:
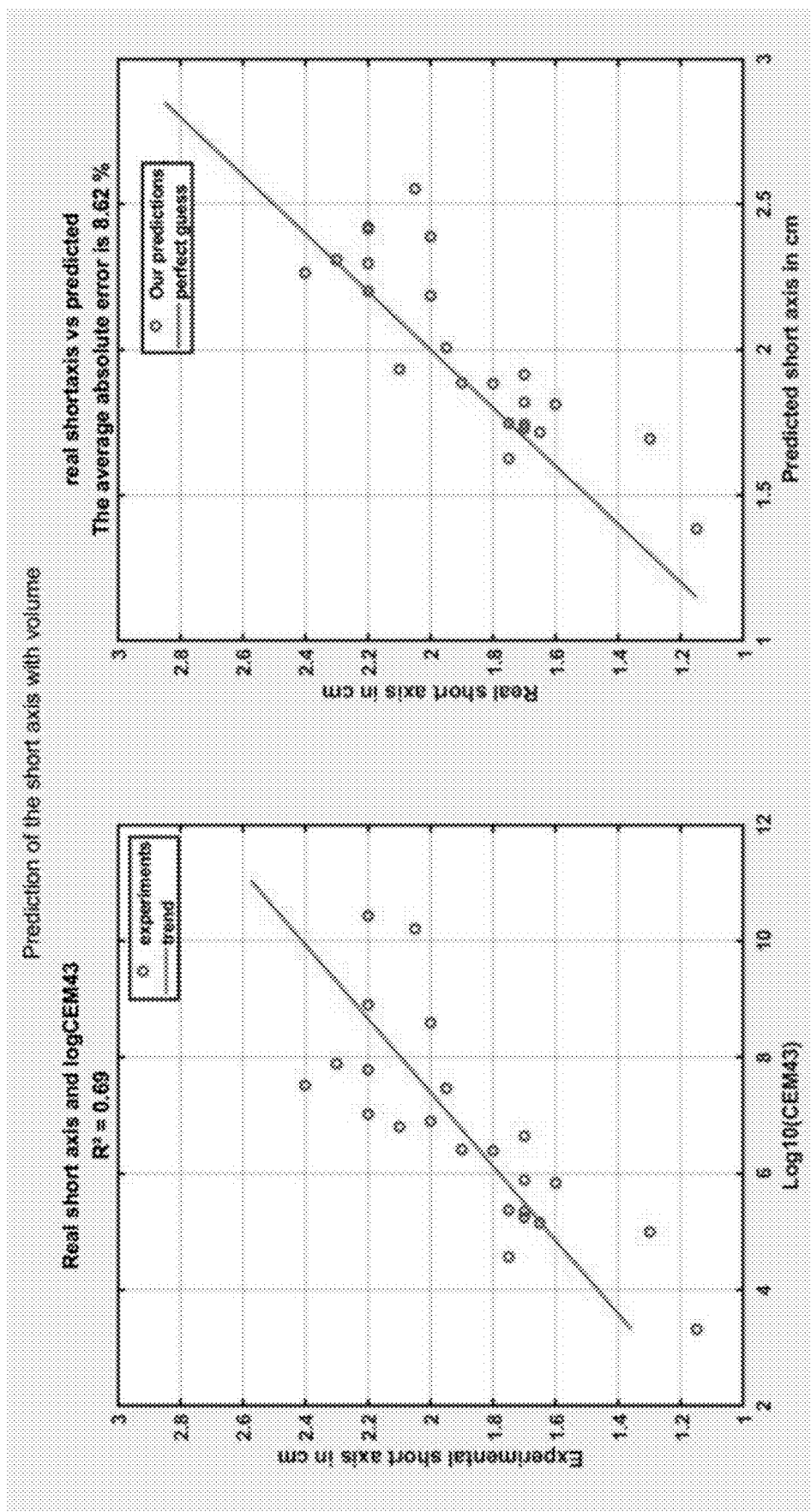
FIG. 7B illustrates trend lines for predicting short axis dimensions of the ablation volume of target tissue based thermal dose of radiometric temperature in accordance with some embodiments.

Referring again to FIG. 3, ablation volume prediction module 330 may predict the dimensions of the predicted ablation volume. For example, assuming that an ablation volume has an ellipsoidal shape having two equal short axes and a third axis longer than the short axes, ablation volume prediction module 330 may predict the length of the short axis and the length of the long axis. As shown in FIG. 7A, the long axis L of the ellipsoidal predicted ablation volume PV may be parallel to the longitudinal axis of switching antenna 200 within predicted ablation volume PV during the ablation, and accordingly, the short axis D of the ellipsoidal predicted ablation volume PV may be perpendicular to the longitudinal axis of switching antenna 200. Ablation volume prediction module 330 may predict the short axis of the ablation volume based on the one or more features extracted from the radiometric signals/thermocouple temperature measurements by feature extraction module 320, as well as information from the datasets accessed by dataset interface module 322. For example, based on the computed thermal dose extracted from the radiometric signal, ablation volume prediction module 330 may analyze the datasets to find correlations, e.g., datasets that include the computed (or similar) thermal dose and corresponding short axis values, and use the correlating dataset to predict the short axis of the ellipsoidal ablation volume of the target tissue. As shown in FIG. 7B, for a computed thermal dose (i.e., Log 10 (CEM43)) of 6, based on the trend line in the graph of real short axis and Log 10 (CEM43) ($R^2$=0.69), ablation volume prediction module 330 may predict a short axis 1.8 cm.

Referring again to FIG. 3, additionally or alternatively, ablation volume prediction module 330 may predict the short and long axes of the ablation volume based on the predicted ablation volume as described above, and an aspect ratio. For example, the volume of an ellipsoid may be calculated as follows:

$$V = \frac{1}{6}\pi * \text{long\_axis} * \text{short\_axis}^2$$

Moreover, the aspect ratio, $$\text{aspect ratio} = \frac{\text{long axis}}{\text{short axis}},$$

is more or less constant. Accordingly, ablation volume prediction module 330 may predict the short and long axes of the ablation volume using the aspect ratio and the predicted ablation volume. By estimating the dimensions of the predicted ablation volume in real-time, as well as the position of the antenna relative to the target tissue, the predicted ablation volume may be displayed as an overlay on the per-CT image, and may grow symmetrically in every direction over time during the ablation procedure.

Figure 8A:
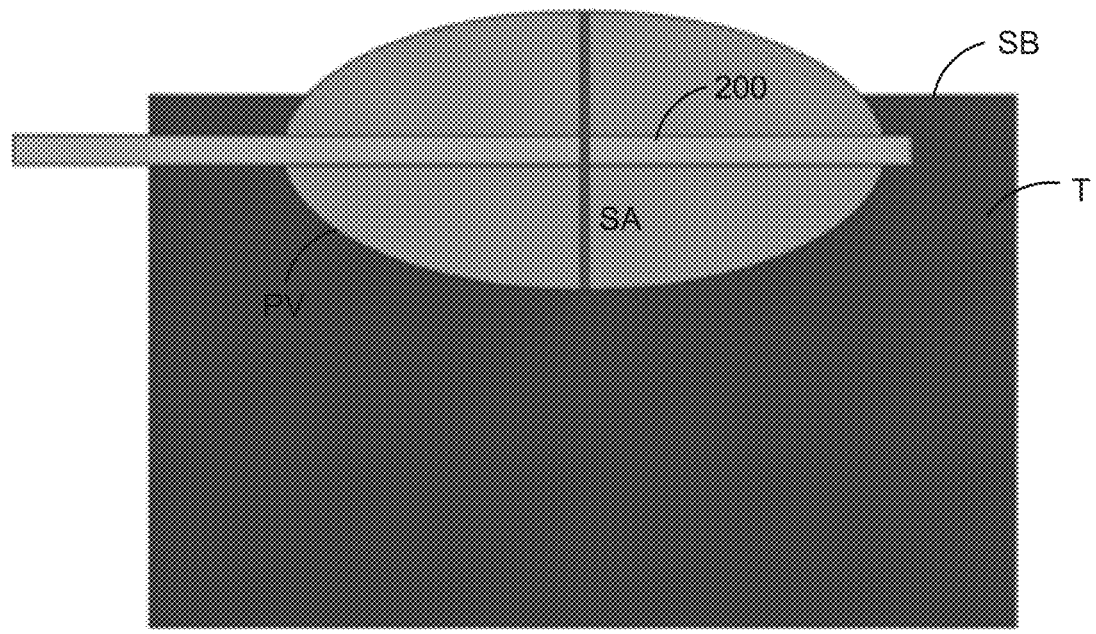
FIGS. 8A and 8B illustrate adaptive prediction of ablation volume of target tissue based on target tissue boundaries in accordance with some embodiments.
Figure 8B:
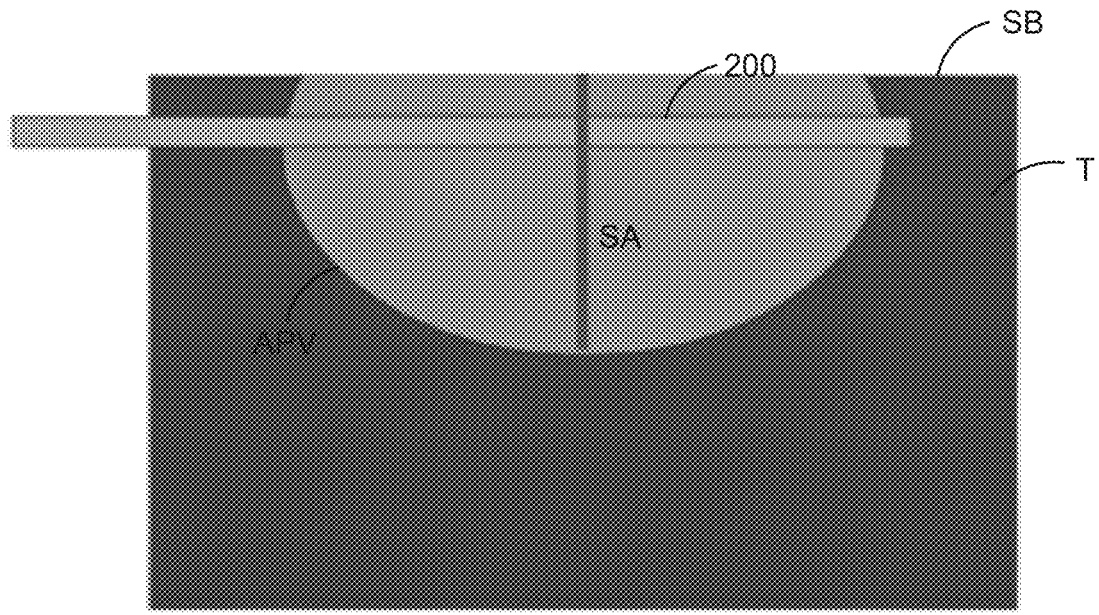

Ablation volume prediction module 330 further may adapt the predicted ablation volume to account for, e.g., the presence and effect of surrounding anatomical structures on the ablation of the target tissue, boundaries/contours of the target tissue computed by image segmentation module 326, etc. For example, the presence of a detected blood vessel adjacent to the target tissue being ablated may cool a surface of the target tissue, thereby affecting the temperature volume of the target tissue, and accordingly the radiometric signal and predicted ablation volume. Moreover, as tissue cannot be ablated beyond its boundaries, ablation volume prediction module 330 may adjust the shape of the predicted ablation volume to accommodate the tissue boundaries. For example, FIG. 8A illustrates an exemplary predicted ablation volume PV having an ellipsoidal shape with short axis SA that would be expected based on the location of switching antenna 200 within target tissue T. However, such a predicted ablation volume shape is impossible due to surface boundary SB of target tissue T. Accordingly, ablation volume prediction module 330 may adjust the shape of the predicted ablation volume to adaptive predicted ablation volume APV to account for surface boundary SB of target tissue T as shown in FIG. 8B. As shown in FIG. 8B, adaptive predicted ablation volume APV may have the same short axis SA value as predicted ablation volume PV of FIG. 8A. Moreover, ablation volume prediction module 330 may adjust the shape of the predicted ablation volume to account for the presence of anatomical structures within/adjacent to the target tissue based on the segmentation of the anatomical structures. For example, growth of the adaptive predicted ablation volume may be restricted to within the target tissue and around the anatomical structures. Accordingly, ablation volume prediction module 330 may predict an adaptive ablation volume using as an input the position of the antenna, the boundary of the target tissue/organ, and the segmentation data of adjacent anatomical structure(s). Moreover, growth of the adaptive predicted ablation volume may be guided by results obtained from previous experiments/simulations. Additionally, or alternatively, growth of the adaptive predicted ablation volume may be determined based at least partially on patient specific simulations created in real-time based on the radiometric signal, as described in further detail below.

Figure 9:
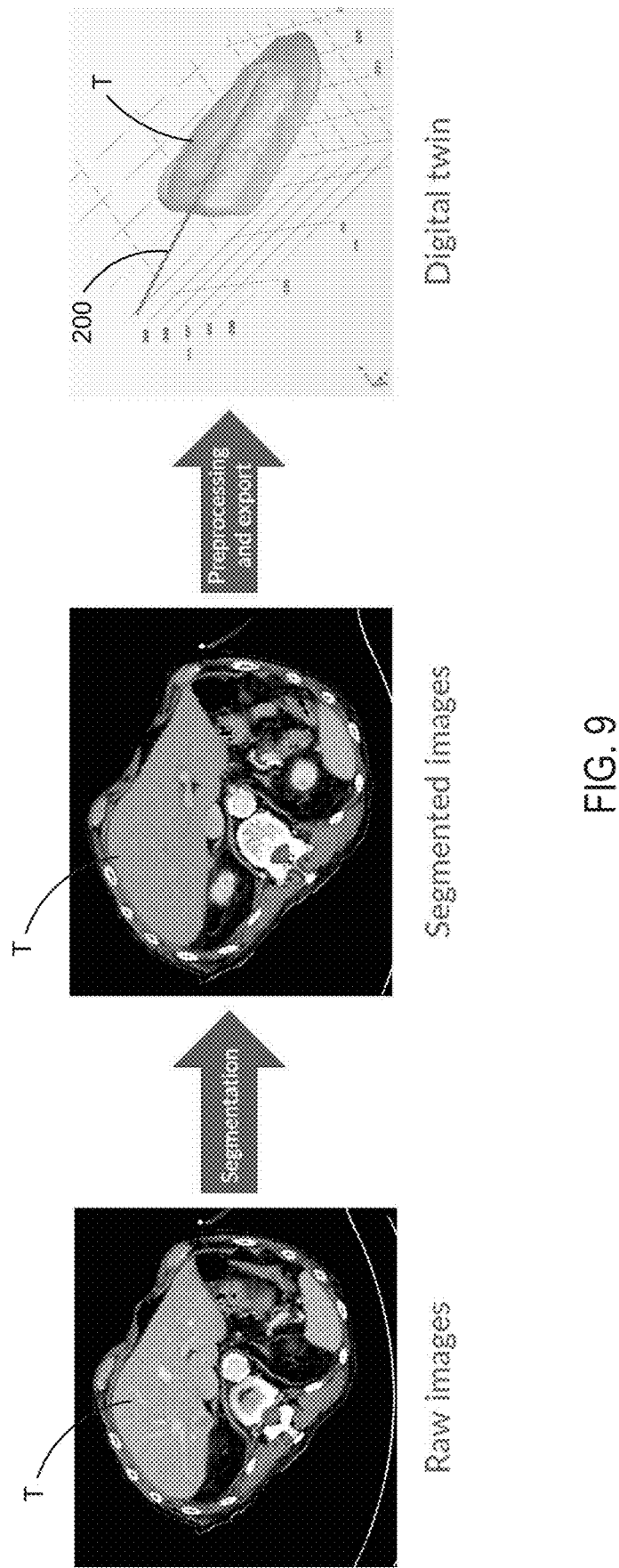
FIG. 9 is a flow chart illustrating generation of a digital twin of patient specific target tissue for patient specific simulation in accordance with some embodiments.

Simulation creation module 332 may be executed by processor 302 for creating a patient specific simulation simulating the growth of the predicted volume of ablated tissue in response to energy emission to the target tissue during an ablation procedure. Specifically, as shown in FIG. 9, simulation creation module 332 may generate a "digital twin," e.g., a 3D reconstruction, of the patient specific target tissue T and the antenna, e.g., antenna 200, based on segmented image data of the patient specific target tissue T. For example, medical images, e.g., pre-CT and per-CT scans, of the patient specific target tissue may be automatically segmented via the segmentation algorithms described above to classify/label the target tissue, e.g., the patient's liver, within the medical images, as well as anatomical structures, e.g., blood vessels surrounding the liver and/or within the liver, within the medical images. However, as the segmented image data may generally not be compatible with simulation software, e.g., COMSOL Multiphysics (made available by COMSOL, Inc., Stockholm, Sweden), simulation creation module 332 may preprocess the segmented image data to ensure compatibility with the simulation software.

Figure 10A:
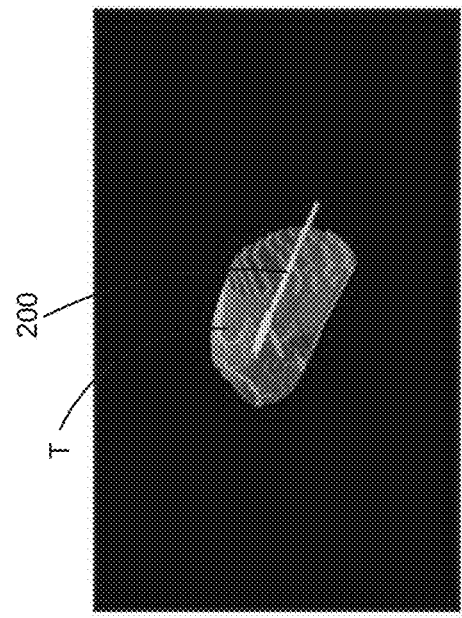
FIGS. 10A to 10D illustrate cropping and smoothing of patient specific target tissue for patient specific simulation in accordance with some embodiments.

For example, as the segmentation volume of the target tissue, e.g., the patient's liver, in the segmented image data may be unnecessarily large, e.g., much larger than the potential ablation zone resulting from an ablation procedure, may be comprised of several anatomical components, and may have an irregular surface, simulation creation module 332 may crop a predetermined volume of the segmented target tissue around the antenna and smooth the edges of the cropped volume, as shown in FIGS. 10A to 10D, to thereby avoid simulating more points than necessary. FIG. 10A illustrates segmented image data generated from per-CT scans of patient specific target tissue T, e.g., the patient's liver, where the entire liver within the medical images and the portion of antenna 200 disposed within the liver are labeled.

Figure 10B:
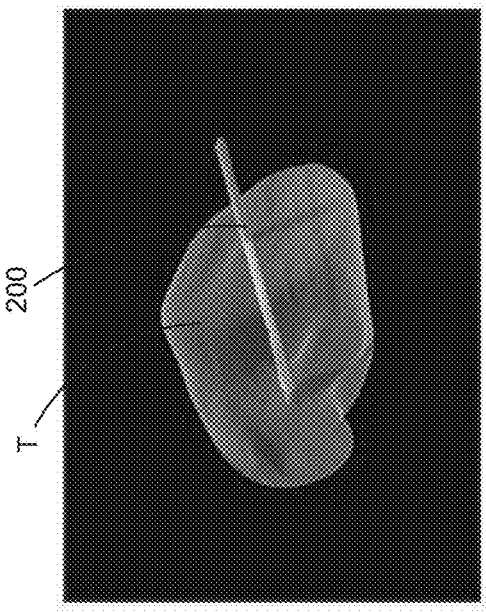
Figure 10C:
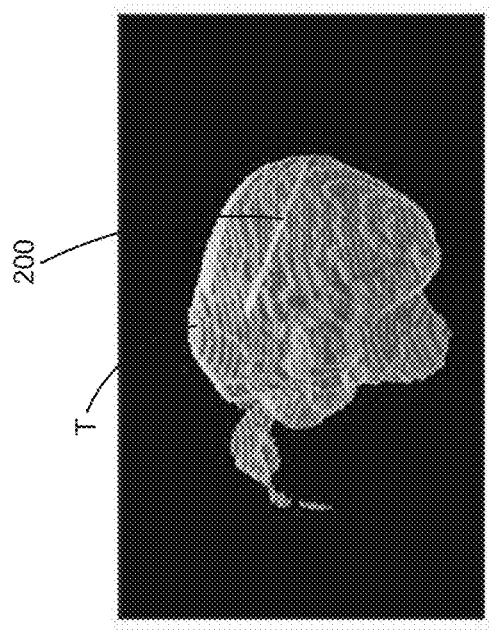
Figure 10D:
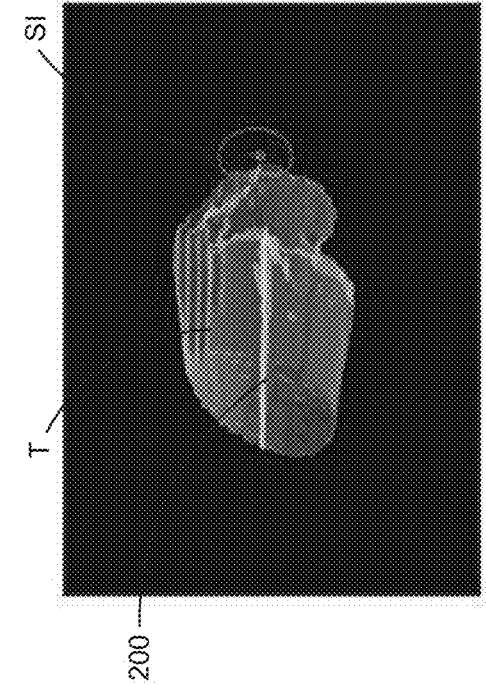

As shown in, FIG. 10B, simulation creation module 332 may crop a predetermined volume of the liver surrounding antenna 200, e.g., the intersection between the liver and a cylinder having a predetermined radius that is aligned with the longitudinal axis of antenna 200. For example, the cylinder may have a radius of 30 mm, such that the volume of the cropped liver is larger than the potential maximum predicted ablation volume. Additionally, as described above, the segmented image data may include several components including, for example, the target cropped volume as well as one or more small segmentation islands SI, as shown in FIG. 10C. Accordingly, simulation creation module 332 may compute one or more connected components of the cropped volume, determine the size of the connected components, and discard any of the connected components smaller than a predetermined size, e.g., small segmentation island SI. The remaining connected component having a size larger than the predetermined size, may then be smoothed, as shown in FIG. 10D. For example, simulation creation module 332 may apply a smoothing filter, e.g., a Gaussian filter with a standard deviation of 3 mm, on the remaining connected component to thereby smooth the irregular surface of the cropped volume. Preferably, the target tissue is first cropped, and then smoothed, to ensure that the edges of the cropped volume as a result of the cropping are also smoothed.

In addition, simulation creation module 332 also may crop and smooth other anatomical structures within the segmented images including, for example, blood vessels within the liver. Smoothing segmented blood vessels is generally more difficult than smoothing a segmented liver, and the resulting cropped and smoothed blood vessels should not form a complex geometry when combined with the cropped and smoothed liver segmentation.

Moreover, the presence of antenna 200 in the per-CT scans may artifact the per-CT scan, such that confidently segmenting the blood vessels in the per-CT scans is essentially impossible. Accordingly, simulation creation module 332 may first register the blood vessels from the pre-CT scans to the per-CT scans. For example, simulation creation module 332 may create a first custom volume of the pre-CT scans and a second custom volume of the per-CT scans, each by converting the liver segmentation therein to a binary mask, e.g., where the voxels outside the liver have a value of 0, and the voxels inside the liver have a value of 1. Registration of the custom volumes of the pre-CT scans and the per-CT scans may be computed by using a B-spline transform. Accordingly, the position of the blood vessels may be registered on the per-CT scans based on the position of the blood vessels in the pre-CT scans as well as the displacement of the voxels of the liver from the pre-CT scan volume to the per-CT scan volume.

Upon registration of the blood vessels on the per-CT scans, simulation creation module 332 may similarly crop a predetermined volume of the blood vessels surrounding antenna 200, e.g., the intersection between the blood vessels and a cylinder having a predetermined radius, e.g., 25 mm, that is aligned with the longitudinal axis of antenna 200, and preferably smaller than the predetermined radius of the cylinder used to crop the liver to ensure that there are no issues with the liver at the boundaries of the cropped volume of the blood vessels. Particularly, if the space between the edge of the cropped liver volume and the edge of the cropped blood vessels volume is too small, it may create issues in the simulation software. After the target cropped volume of the blood vessels is obtained, simulation creation module 332 may then smooth the cropped blood vessels volume. For example, simulation creation module 332 may resample the blood vessel segmentation of the cropped volume to have an isometric spacing of, e.g., 0.5 mm, apply a morphological closing with a kernel of, e.g., 3 mm, resample the blood vessel segmentation of the cropped volume to have an isometric spacing of, e.g., 0.1 mm, and apply a Gaussian filter with a parameter of, e.g., 0.4 mm. The resampling of the segmentation data improves filtering. Moreover, simulation creation module 332 may similarly remove small segmentation islands in the blood vessels segmentation, e.g., by computing the size of all connected components of the blood vessels segmentation, and discard any connected components smaller than a predetermined size, e.g., smaller than 250 voxels. Accordingly, the cropped and smoothed volumes of the liver and blood vessels may be combined to form a 3D volume of the target tissue surrounding the antenna for patient specific simulation. As will be understood by a person having ordinary skill in the art, simulation creation module 332 may crop and smooth other anatomical structures within the segmented images adjacent to the target tissue, e.g., the liver, including, for example, airways, cancerous tissue, etc.

Moreover, as ablated tissue may contract during an ablation procedure, e.g., the tissue "burns" as a result of being ablated, the contraction creates a movement in the ablation zone, such that the predicted ablation volume may be underestimated if the contraction is not taken into account. Accordingly, simulation creation module 332 may measure contraction of the target tissue as a result of an ablation procedure, as shown in FIGS. 11A to 11D. For example, simulation creation module 332 may compute the contraction from the registration between pre-operative scans of the target tissue prior to an ablation procedure, and post-operative scans of the same target tissue after the ablation procedure. The pre-operative and post-operative scans are first segmented, e.g., using the segmentation algorithms described above, to thereby classify/label the liver and the blood vessels within the medical images. For example, FIG. 11A illustrates a segmented pre-operative scan.

Preferably, the volumes of the pre-operative and post-operative scans are registered via a variant of a label-based registration, as opposed to intensity-based registration. For example, simulation creation module 332 may create a first custom volume of the pre-operative scans and a second custom volume of the post-operative scans, each by converting the liver segmentation and the blood segmentation therein to a binary mask where the custom volumes are defined as:

$$V_{custom} = \text{liver} + 2 * \text{blood\_vessel}$$

Where the voxels outside the liver and the blood vessels have a value of 0, the voxels inside the liver but outside the blood vessels have a value of 1, the voxels inside the blood vessels but outside the liver have a value of 2, and the voxels inside the liver and the blood vessels have a value of 3, as shown in FIG. 11B.

Registration of the custom volumes of the pre-operative scans and the post-operative scans may be computed by using a B-spline transform, as shown in FIG. 11C, and the contraction may be computed by forcing the displacement of the voxels to be zero at the radiative element position, e.g., antenna 200, as shown in FIG. 11D. Forcing the displacement of the voxels to be zero at antenna 200 takes into account the patient displacement between the different scans. The position of antenna 200 may be determined based on segmentation of the antenna, as described above. Accordingly, simulation creation module 332 may create a patient specific simulation that simulates the predictive ablation volume that takes into account contraction of the target tissue as a result of the ablation procedure, as well as the tissue boundaries, properties of the tissue surrounding the antenna, and the effects of surround anatomical structures to thereby enhance the prediction of the true ablation zone. The patient specific simulated contracted ablation zone further may be displayed to the user.

Figure 12A:
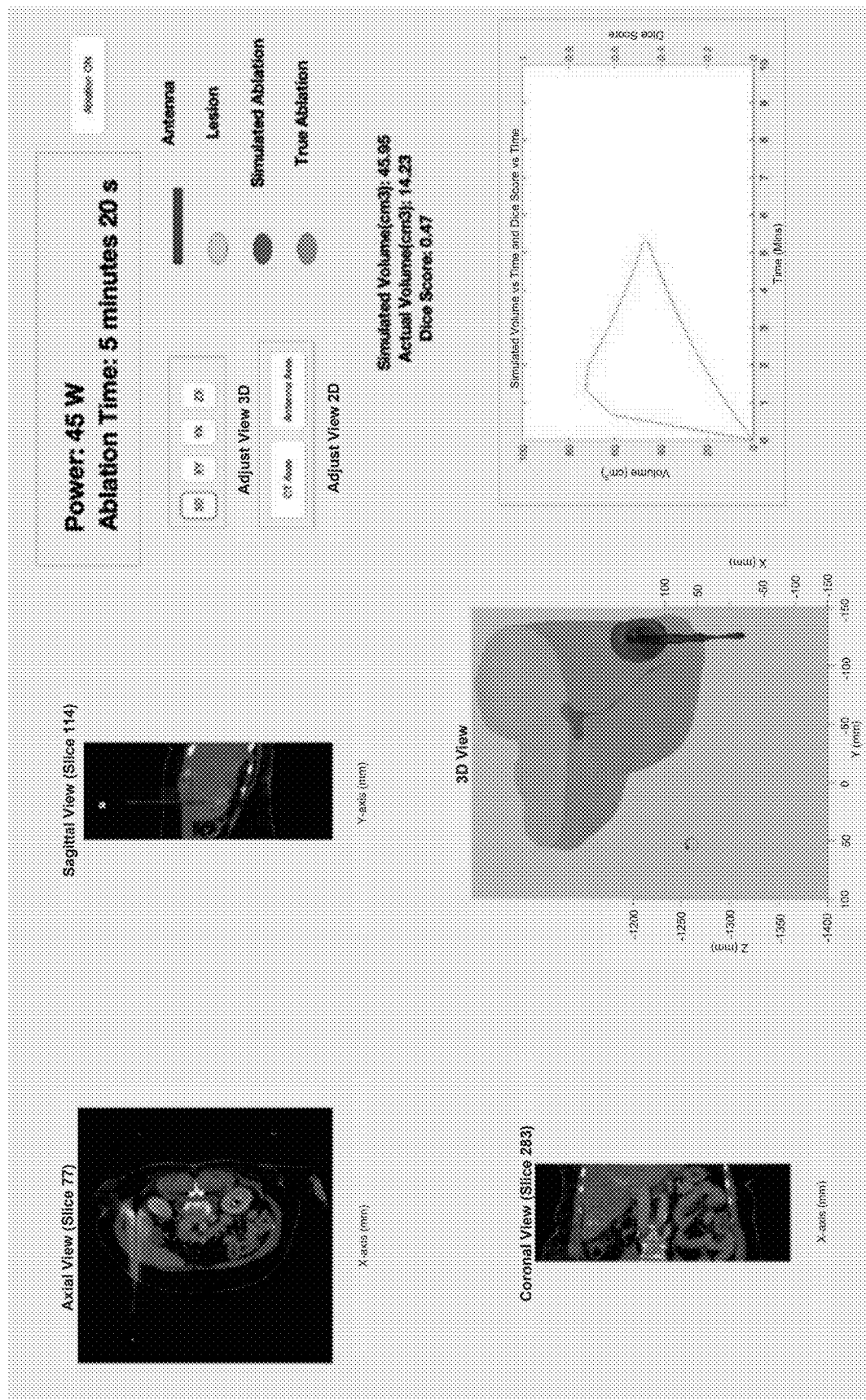
FIG. 12A illustrates another exemplary graphical user interface for displaying adaptive predicted ablation volume of target tissue in accordance with some embodiments

FIG. 12A illustrates an exemplary graphical user interface, e.g., user interface 308, displaying the adaptive predicted ablation volume in real-time during ablation of liver tissue. As shown in FIG. 12A, the graphical user interface may display various views of the target tissue, e.g., axial, sagittal, coronal, 3D views, including the labeled antenna, labeled target tissue, labeled lesion, and the labeled predicted ablation volume. Moreover, the user interface may display additional information including, for example, the radiometric signal, the value of the predicted ablation volume, the computed dimensions of the predicted ablation volume, ablation time, power level of ablation energy, etc. As described above, ablation volume prediction module 330 may simulate growth of the adaptive predicted ablation volume using a physics-based model that uses as an input, a 3D model of the antenna, the segmentation of the tissue/organ, and ablation parameters, as well as segmentation of anatomical structures, which may be displayed as shown in FIG. 12B.

Figure 12B:
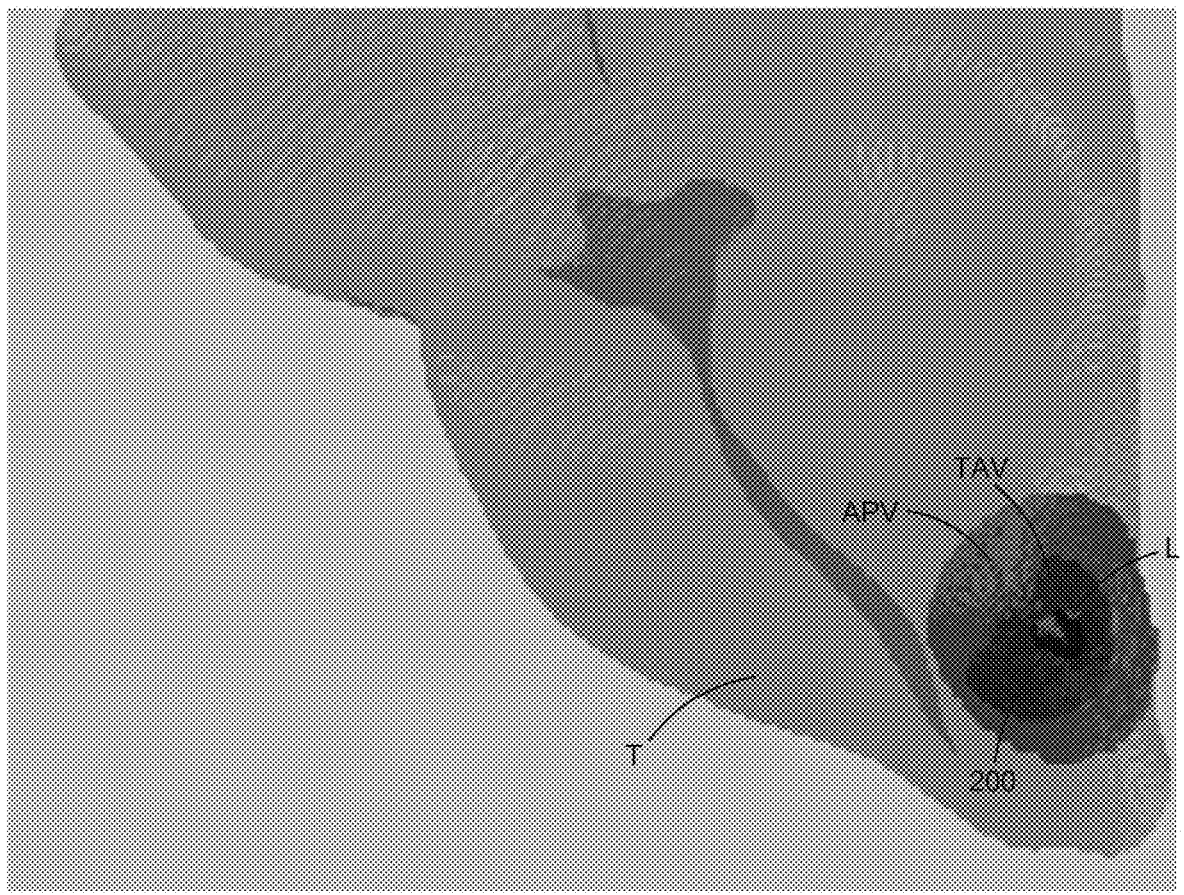
FIG. 12B illustrates growth of the adaptive predicted ablation volume of target tissue over time.

FIG. 12B illustrates the directional growth of the adaptive predicted ablation volume over time compared with the actual ablation volume, e.g., true ablation volume TAV generated based on post-CT images. For example, in the liver, contrast enhanced CT may provide information of true ablation volume TAV, which may be displayed as an overlay with adaptive predicted ablation volume APV to facilitate validation of the accuracy of adaptive predicted ablation volume APV. As shown in FIG. 12B, the growth of true ablation volume TAV may not be symmetric about switching antenna 200 within lesion L due to the boundary of tissue T, e.g., a liver, which limits the growth in one direction. For example, the boundary of tissue T causes true ablation volume TAV to grow more on the left side, which is accurately captured by adaptive predicted ablation volume APV, as shown in FIG. 12B, thereby validating the accuracy of adaptive predicted ablation volume APV.

As described above, additional segmented anatomical structures, e.g., a blood vessel that cools adjacent tissue, would further affect the non-symmetric shape of adaptive predicted ablation volume APV. As will be understood by a person having ordinary skill in the art, the predicted ablation volume need not be computed prior to computation of the adaptive predicted ablation volume. For example, the adaptive predicted ablation volume and the predicted ablation volume may be computed simultaneously, and/or the adaptive predicted ablation volume may be computed prior to the predicted ablation volume.

Referring again to FIG. 3, overlay generation module 334 may be executed by processor 302 for generating overlaid images for display to provide feedback and guide a user during the ablation procedure. As described above, the lesion is labeled on the pre-CT image and the antenna is labeled on the per-CT image, image segmentation module 326 may segment and label the target tissue, e.g., the target organ, on both the pre-CT image and the per-CT image, such that overlay generation module 334 may then execute a registration toolbox to register the per-CT image and the pre-CT image based on the segmented target tissue in both the per-CT image and the pre-CT image. Once registration is complete, overlay generation module 334 may then overlay the labeled lesion of the pre-CT image on the per-CT image, such that the overlaid pre-CT image may include the labeled antenna, labeled target tissue, and labeled lesion.

Figure 13:
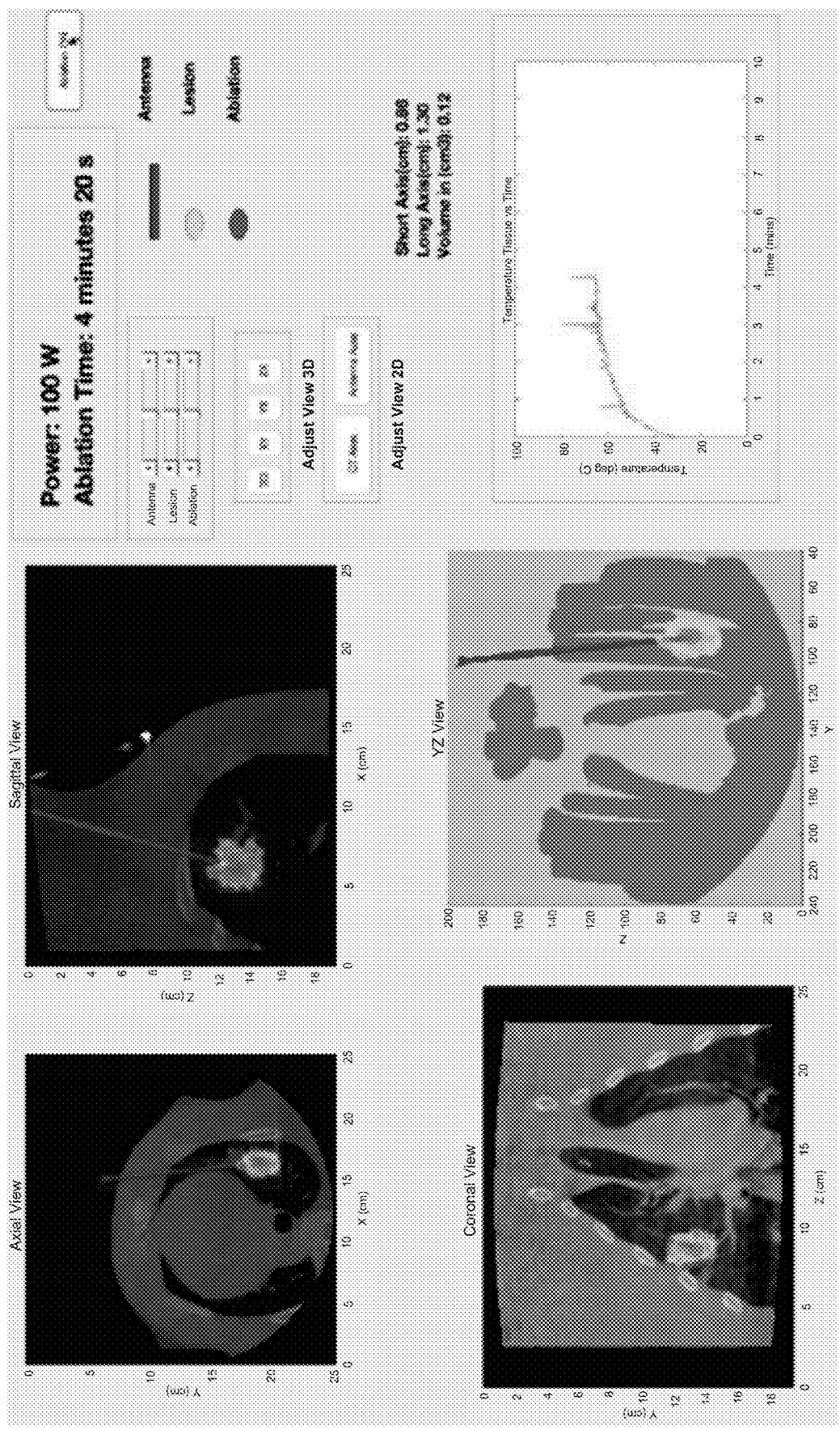
FIG. 13 illustrates an exemplary graphical user interface for displaying predicted ablation volume of target tissue based on radiometric signals in accordance with some embodiments.

Moreover, overlay generation module 334 further may overlay the overlaid per-CT image with the predicted ablation volume in real-time, e.g., based on the computed dimensions of the predicted ablation volume, as shown in FIG. 13. FIG. 13 shows an exemplary graphical user interface, e.g., user interface 308, displaying various views of the target tissue, e.g., axial, sagittal, coronal, YZ views, including the labeled antenna, labeled target tissue, labeled lesion, and the labeled predicted ablation volume. Moreover, the user interface may display additional information including, for example, 3D views, the radiometric signal, the value of the predicted ablation volume, the computed dimensions of the predicted ablation volume, ablation time, power level of ablation energy, etc.

Figure 14:
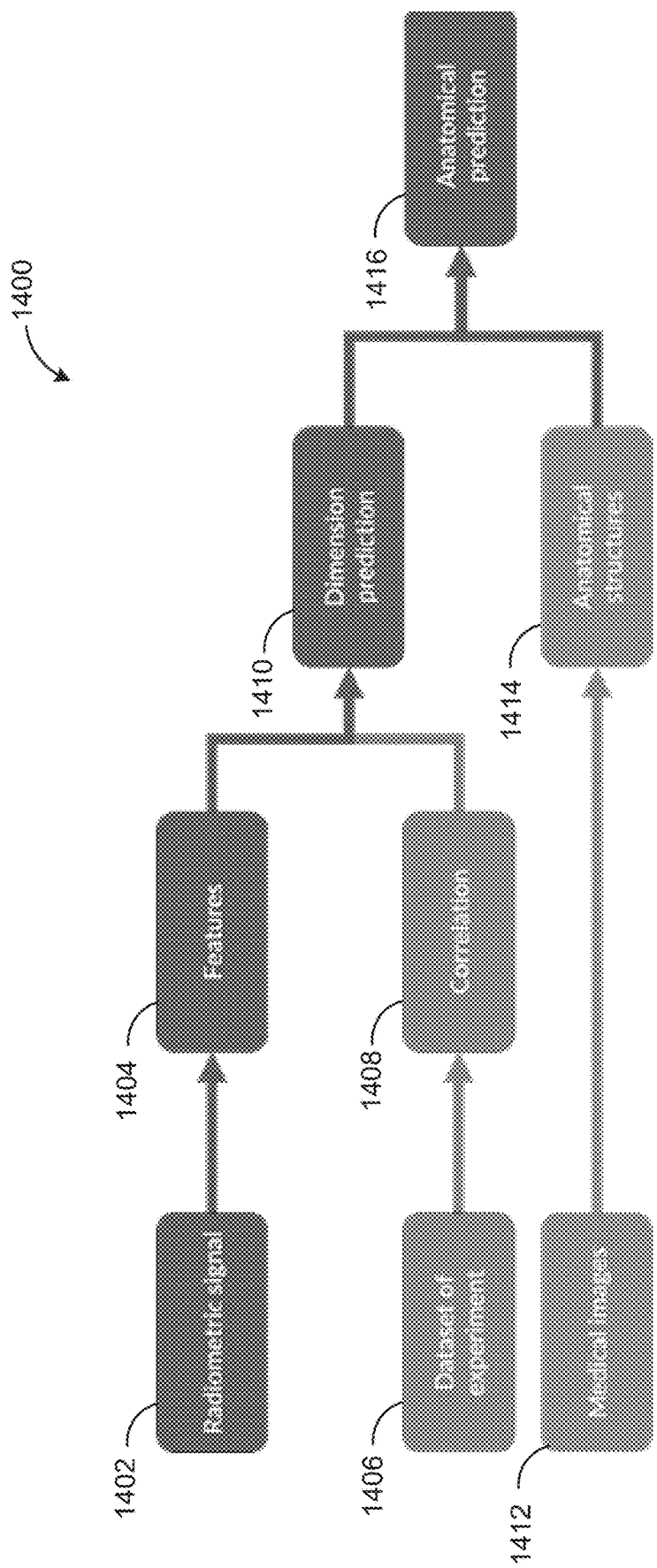
FIG. 14 is a flow chart illustrating exemplary method steps for adaptively predicting ablation volume of target tissue in accordance with some embodiments.

Referring now to FIG. 14, a flow chart summarizing exemplary method 1400 for adaptively predicting ablation volume of target tissue in accordance with the principles of the present disclosure is provided. Steps 1402-1410 may be used to predict the dimensions of a predicted volume of ablation of target tissue based on radiometric signals received from radiometer 24 and/or temperature measurements provided by thermocouple 210, and correlating datasets of results from previous experiments/simulations, as described above. For example, at step 1402, controller 300 may receive radiometric signals from radiometer 24, e.g., when T/R switch 16 is in the measurement state such that radiometer 24 receives temperature measurement from switching antenna 200, e.g., from the main antenna when switch bias diplexer 18 is in the main antenna state and/or the reference termination when switch bias diplexer 18 is in the reference termination state. As described above, the radiometric signal may be filtered using at least one of an anti-spike filter or a smoothing filter. Additionally, or alternatively, at step 1402, controller 300 may receive the voltages returned by thermocouple 210 indicative of the temperature of tissue surrounding the antenna, and convert these voltages to temperature values.

At step 1404, controller 300 may extract one or more features of the radiometric signal/thermocouple tissue temperature, e.g., the area under the temperature curve, the maximum temperature, the thermal dose, the initial slope, the average temperature rise, etc. Moreover, at step 1406, controller 300 may access a database of datasets of results from previous experiments/simulations, and at step 1408, controller 300 may analyze the datasets to find correlations with the one or more extracted features, e.g., a correlating dataset with predicted ablation volumes for given thermal dose values and/or short axis values for given thermal dose values. At step 1410, controller 300 may predict the dimensions of the predicted ablation volume using information derived from the correlating dataset, e.g., a trend line. Additionally, or alternatively, controller 300 may predict the dimensions of the predicted ablation volume based on patient specific simulations created in real-time during an ablation procedure, as described above. Steps 1406 and 1408 may be precomputed, whereas steps 1402, 1404, and 1410 may be performed in real-time.

Moreover, based on predicted ablation volume dimensions obtained at step 1410, steps 1412-1416 may be used to compute an anatomically correct prediction, e.g., to take in account target tissue boundaries and/or the presence of anatomical structures such as airways, blood vessels, bile ducts, etc., as described above. For example, at step 1412, controller 300 may receive medical images of the target tissue, and at step 1414, controller may execute one or more segmentation algorithms to automatically segment the target tissue as well as anatomical structures within the medical images. At step 1416, controller 300 may predict the adaptive volume of ablation of the target tissue that takes into account the segmented anatomical structure(s), which may then be displayed as an overlay on the medical image comprising the labeled target tissue, labeled lesion, labeled antenna, and labeled anatomical structure(s). Moreover, as described above, controller 300 may predict the adaptive volume of ablation of the target tissue based at least partially on the patient specific tissue properties parameters estimated based on the radiometric signal/thermocouple tissue temperature and correlated datasets including corresponding average tissue properties parameter values, as described above. Steps 1412 and 1414 may be performed prior to the ablation procedure, whereas steps 1410 and 1416 may be performed in real-time.

Figure 15A:
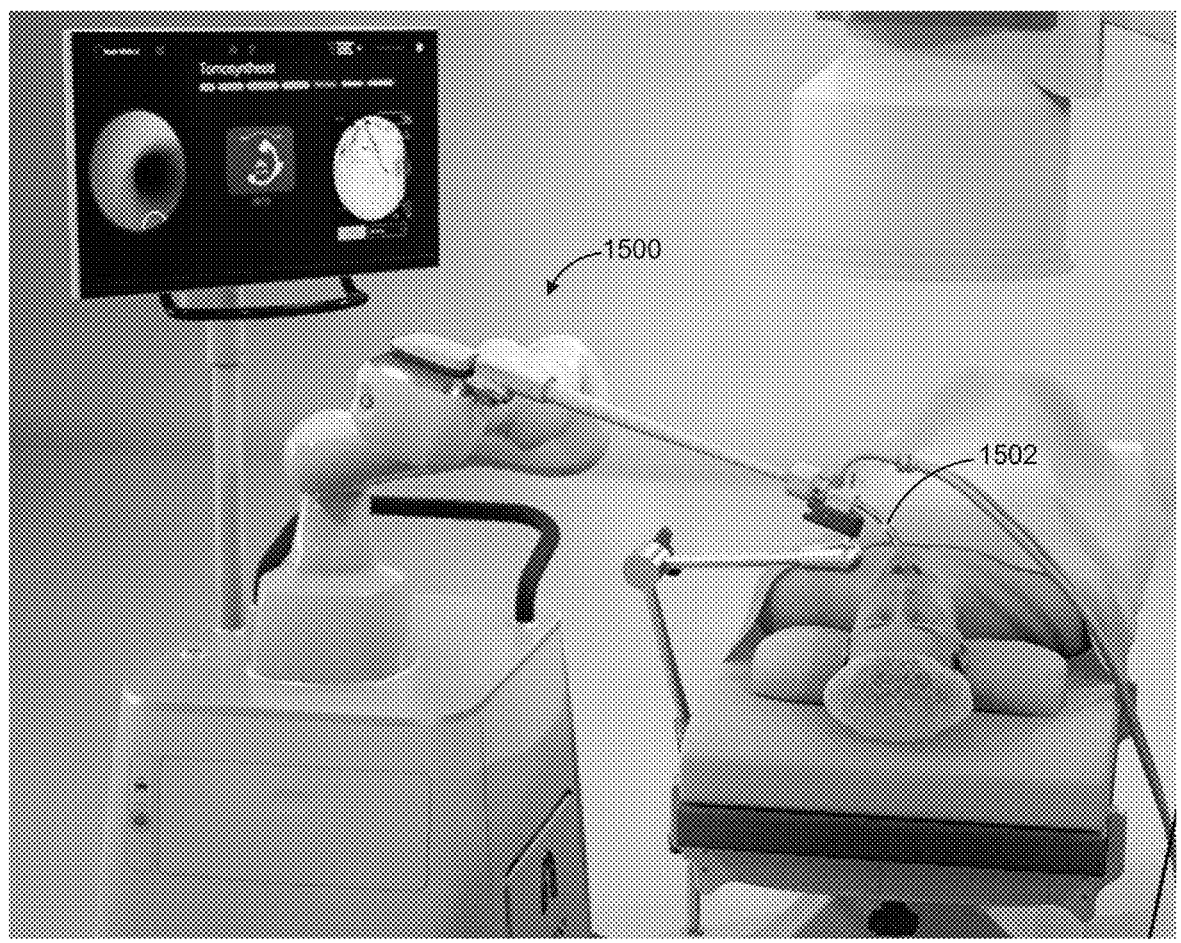
FIGS. 15A and 15B illustrate an exemplary robot system for delivering the radiometer antenna of the microwave ablation system to the target tissue in accordance with some embodiments.
Figure 15B:
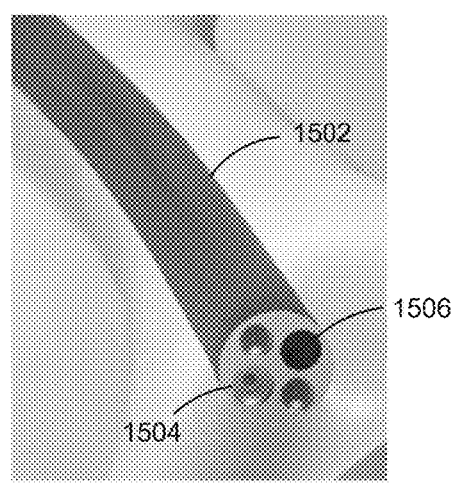

Referring now to FIGS. 15A and 15B, an exemplary robotic navigation system that may be used to delivery switching antenna 200 to the target tissue is provided. Robotic navigation system 1500 may be Galaxy System™ (available by Noah Medical, San Carlos, California) having delivery catheter 1502 configured to navigate through the patient's anatomy to the target tissue, e.g., lung tissue. As shown in FIG. 15B, delivery catheter 1502 may include scope 1504 configured to generate video data, and lumen 1506 sized and shaped to receive the catheter of system 10, e.g., switching antenna 200 and cable 20, therethrough. Accordingly, switching antenna 200 may be delivered through lumen 1506 of delivery catheter 1502 via robotic navigation system 1500 to perform an ablation procedure and measure temperature of the target tissue as described above.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for predicting ablation volume of tissue, the system comprising a controller having instructions that, when executed by one or more processors of the controller, cause the controller to:
receive information indicative of temperature of a tissue being ablated via an antenna;
extract one or more features of the temperature of the tissue from the information, the one or more features comprising at least one of an area under a curve of the temperature of the tissue, a maximum temperature of the tissue, a thermal dose of the temperature of the tissue, an initial slope of the temperature of the tissue, or an average temperature rise of the tissue; and
execute an ablation volume prediction algorithm to predict the volume of ablation of the tissue based on the extracted one or more features and a trend line derived from a correlated dataset of ablation volumes associated with the extracted one or more features.

2. The system of claim 1, wherein the information indicative of temperature of the tissue being ablated via the antenna comprises a radiometric signal generated by the antenna.

3. The system of claim 2, wherein the controller is programmed to use an anti-spike filter on the radiometric signal to remove one or more incorrect points within the radiometric signal, the anti-spike filter comprising at least one of a moving minimum or an algorithm based on a first derivative.

4. The system of claim 2, wherein the controller is programmed to use a smoothing filter on the radiometric signal to generate a smoother signal, the smoothing filter comprising at least one of a Kalman filter or a moving average.

5. The system of claim 2, wherein the controller is programmed to detect an uncontrolled increase in temperature of the tissue based on the radiometric signal.

6. The system of claim 2, where the controller is programmed to detect a presence of a heat sink based on the radiometric signal and a dataset of simulation results.

7. The system of claim 1, wherein the information indicative of temperature of the tissue being ablated via the antenna comprises a voltage returned by a thermocouple disposed on an external surface of the antenna.

8. The system of claim 1, wherein the controller is programmed to take a logarithm of cumulative equivalent minutes at 43° C. to extract the thermal dose of the tissue.

9. The system of claim 1, wherein the controller is programmed to calculate a short axis and a long axis of an ellipsoidal ablation volume corresponding with the predicted volume of ablation of the tissue, the long axis parallel to a longitudinal axis of the antenna.

10. The system of claim 9, wherein the controller is programmed to calculate the short axis of the ellipsoidal ablation volume based on the extracted thermal dose and a trend line derived from a correlated dataset of short axes associated with the extracted thermal dose.

11. The system of claim 9, wherein the controller is programmed to calculate the short axis and the long axis of the ellipsoidal ablation volume based on an aspect ratio of the predicted volume of ablation of the tissue.

12. The system of claim 1, wherein the controller is programmed to:
compare the extracted initial slope of the temperature of the tissue with a dataset of initial slope values and associated electromagnetic tissue properties to determine one or more electromagnetic properties of the tissue; and
determine a type of the tissue based on the determined one or more electromagnetic properties of the tissue.

13. The system of claim 12, wherein the controller is programmed to determine whether the tissue is healthy tissue or cancerous tissue based on the determined one or more electromagnetic properties of the tissue.

14. The system of claim 12, wherein the controller is programmed to:
cause the antenna to emit energy to the tissue at a predetermined level for a predetermined time period, the predetermined level and the predetermined time period insufficient to damage the tissue,
wherein the initial slope of the temperature of the tissue is extracted from the information received responsive to the energy emitted to the tissue at the predetermined level for the predetermined time period.

15. The system of claim 12, wherein the controller is programmed to:
estimate one or more tissue property parameters of the tissue based on the information indicative of temperature of the tissue being ablated and a correlated dataset of tissue temperatures and corresponding average tissue property parameter values; and
adapt the predicted volume of ablation of the tissue based on the one or more tissue property parameters.

16. The system of claim 1, wherein the controller is programmed to determine at least one of water content of the tissue or physical properties of surrounding tissue based on the extracted initial slope of the temperature of the tissue.

17. The system of claim 1, wherein the controller is programmed to cause a display to display the predicted volume of ablation of the tissue.

18. The system of claim 17, wherein the controller is programmed to:
receive a medical image comprising the tissue and the antenna;
execute a segmentation algorithm to segment the tissue and the antenna in the medical image;
label the segmented tissue and antenna on the medical image; and
cause the display to display the predicted volume of ablation of the tissue overlaid on the labeled medical image comprising the labeled segmented tissue and antenna.

19. The system of claim 18, wherein the medical image comprises a CT scan image, a CBCT scan image, a tomosynthesis image based on X-ray, an MRI image, or an echographic B-mode image.

20. The system of claim 18, wherein the controller is programmed to:
receive a pre-operative medical image comprising the tissue, the pre-operative medical image comprising a labeled lesion;
execute a segmentation algorithm to segment the tissue in the pre-operative medical image;
execute a registration toolbox to register the labeled medical image and the pre-operative medical image based on the segmented tissue in the labeled medical image and the pre-operative medical image; and
overlay the labeled lesion on the registered labeled medical image,
wherein the displayed predicted volume of ablation of the tissue is overlaid on the registered labeled medical image comprising the labeled lesion.

21. The system of claim 18, wherein the medical image comprises one or more anatomical structures, and wherein the controller is programmed to:
execute a segmentation algorithm to segment the one or more anatomical structures in the medical image; and
label the segmented one or more anatomical structures on the medical image,
wherein the displayed predicted volume of ablation of the tissue is overlaid on the labeled medical image comprising the labeled segmented tissue, antenna, and one or more anatomical structures.

22. The system of claim 21, wherein the controller is programmed to:
determine a boundary of the tissue based on the segmented tissue; and
determine a shape of the predicted volume of ablation of the tissue based on the boundary of the tissue, a location of the segmented antenna, a location of the segmented one or more anatomical structures, and a dataset of simulation results,
wherein the displayed predicted volume of ablation of the tissue comprises the determined shape.

23. The system of claim 21, wherein the one or more anatomical structures comprises at least one of an airway, a blood vessel, or bile ducts.

24. The system of claim 17, wherein the controller is programmed to create a patient specific simulation simulating growth of the predicted volume of ablation of the tissue over time.

25. The system of claim 24, wherein the controller is programmed to:
compute a contraction of the tissue based on a registration of pre-operative and post-operative scans of the tissue; and
adapt the patient specific simulation based on the contraction of the tissue.

26. The system of claim 25, wherein the controller is programmed to:
execute a segmentation algorithm to segment the tissue and one or more anatomical structures within the pre-operative and post-operative scans;
convert the segmented tissue and one or more anatomical structures within the pre-operative and post-operative scans to a binary mask to create custom volumes of the pre-operative and post-operative scans;
register the custom volume of the pre-operative scans with the custom volume of the post-operative scans; and
force displacement of voxels corresponding to the antenna to zero to compute the contraction of the tissue.

27. The system of claim 24, wherein the controller is programmed to:
receive medical images comprising the tissue, one or more anatomical structures within the tissue, and the antenna;
execute a segmentation algorithm to segment the tissue, the one or more anatomical structures, and the antenna in the medical images;
crop predetermined volumes of the tissue and the one or more anatomical structures from the segmented medical images based on a position of the antenna within the segmented medical images; and smooth the cropped volumes of the tissue and the one or more anatomical structures, wherein the patient specific simulation is created based on the cropped and smoothed volumes of the tissue and the one or more anatomical structures.

28. The system of claim 27, wherein the one or more anatomical structures comprise one or more blood vessels, and wherein the medical images comprise pre-operative medical images comprising the tissue and the one or more blood vessels and per-operative medical images obtained during an ablation procedure and comprising the tissue and the antenna, the controller further programmed to:

register the one or more blood vessels from the pre-operative medical images to the per-operative medical images to crop the predetermined volume of the blood vessels based on the position of the antenna, wherein the predetermined cropped volume of the blood vessels is smaller than the predetermined cropped volume of the tissue.

29. The system of claim 24, wherein the controller is programmed to determine a shape of the predicted volume of ablation of the tissue at least partially based on the patient specific simulation.

30. The system of claim 1, wherein the ablation volume prediction algorithm is configured to predict the volume of ablation of the tissue based on a power level of energy used to ablate the tissue.

* * * * *